US012751861B2

(12) United States Patent
Grüebler et al.

(10) Patent No.: US 12,751,861 B2
(45) Date of Patent: Oct. 6, 2026

(54) GRASPING STRUCTURES FOR MEMBRANE REMOVAL

(71) Applicant: Alcon Inc., Fribourg (CH)

(72) Inventors: Reto Grüebler, Greifensee (CH); Luca Palmerini, Basel (CH)

(73) Assignee: Alcon Inc., Fribourg (CH)

( * ) Notice: Subject to any disclaimer, the term of this patent is extended or adjusted under 35 U.S.C. 154(b) by 79 days.

(21) Appl. No.: 18/533,465

(22) Filed: Dec. 8, 2023

(65) Prior Publication Data

US 2024/0197527 A1 Jun. 20, 2024

Related U.S. Application Data

(60) Provisional application No. 63/387,350, filed on Dec. 14, 2022.

(51) Int. Cl.
*A61F 9/007* (2006.01)

(52) U.S. Cl.
CPC ................................ *A61F 9/00736* (2013.01)

(58) Field of Classification Search
CPC .. A61F 9/00736; A61F 9/007; A61F 9/00709; A61F 9/00745; A61F 9/00754; A61F 9/00763; A61B 17/30; A61B 17/32056; A61B 17/29; A61B 2017/305; A61B 2017/2926; A61B 2017/2945
See application file for complete search history.

(56) References Cited

U.S. PATENT DOCUMENTS

| | | | |
|---|---|---|---|
| 5,632,746 | A | 5/1997 | Middleman |
| 6,908,476 | B2 | 6/2005 | Jud |
| 6,945,984 | B2 | 9/2005 | Arumi |
| 9,320,534 | B2 | 4/2016 | Vezzu |
| 9,827,141 | B2 | 11/2017 | Schaller |
| 10,406,027 | B2 | 9/2019 | Grueebler et al. |
| 10,500,090 | B2 | 12/2019 | Gunn et al. |
| 10,729,504 | B2 | 8/2020 | Schaller |
| 10,973,682 | B2 | 4/2021 | Vezzu et al. |
| 11,224,539 | B2 | 1/2022 | Grueebler |

(Continued)

FOREIGN PATENT DOCUMENTS

| | | | |
|---|---|---|---|
| CN | 111214325 | A | 6/2020 |
| CN | 217660411 | U | 10/2022 |

(Continued)

OTHER PUBLICATIONS

Alcon Surgical Retina Product Catalog, 2019 (36 pages).

*Primary Examiner* — Katherine H Schwiker
(74) *Attorney, Agent, or Firm* — Patterson + Sheridan, LLP

(57) ABSTRACT

A surgical instrument includes a flexible outer grasping member and a flexible inner grasping member for peeling a membrane from the retina of a patient's eye. The surgical instrument includes a handle and at least one actuator. An outer tube has a proximal end mounted to the handle. The outer and inner grasping members extend outwardly from a distal end of the outer tube, or are configured to extend outwardly from the distal end of the outer tube. The at least one actuator may be used to move at least one of the outer grasping member and the inner grasping member relative to the other such that the inner grasping member and the outer grasping member are brought together to grasp the retinal membrane.

8 Claims, 16 Drawing Sheets

(56) References Cited

U.S. PATENT DOCUMENTS

| | | | |
|---|---|---|---|
| 11,490,915 | B2 | 11/2022 | Abt |
| 11,751,909 | B2 | 9/2023 | Schaller |
| 11,759,237 | B2 | 9/2023 | Schaller |
| 2006/0116703 | A1 | 6/2006 | Glaser |
| 2008/0183199 | A1 | 7/2008 | Attinger |
| 2012/0116435 | A1 | 5/2012 | Nallakrishnan |
| 2013/0073054 | A1 | 3/2013 | Olsen et al. |
| 2014/0135820 | A1 | 5/2014 | Schaller et al. |
| 2014/0172010 | A1* | 6/2014 | Vezzu ................ A61F 9/00736 606/207 |
| 2015/0297406 | A1 | 10/2015 | Braun et al. |
| 2016/0262931 | A1 | 9/2016 | Bhattacharjee |
| 2016/0296246 | A1 | 10/2016 | Schaller |
| 2019/0183681 | A1* | 6/2019 | Schaller ................. A61F 9/013 |
| 2019/0216643 | A1 | 7/2019 | Olson |
| 2020/0069465 | A1 | 3/2020 | Gunn et al. |
| 2020/0337899 | A1 | 10/2020 | Charles |
| 2020/0375844 | A1 | 12/2020 | Maschio et al. |
| 2021/0113378 | A1 | 4/2021 | Kahook et al. |
| 2021/0121326 | A1* | 4/2021 | Kahook ........... A61B 17/32053 |
| 2021/0346199 | A1 | 11/2021 | Stappler et al. |
| 2022/0031509 | A1 | 2/2022 | Tazawa |
| 2022/0117779 | A1 | 4/2022 | Hallen |

FOREIGN PATENT DOCUMENTS

| | | | |
|---|---|---|---|
| CN | 218220436 | U | 1/2023 |
| EP | 3695809 | A1 | 8/2020 |
| EP | 4162905 | A1 | 4/2023 |

* cited by examiner

GRASPING STRUCTURES FOR MEMBRANE REMOVAL

BACKGROUND

The internal limiting membrane (ILM) is a thin transparent membrane positioned between the vitreous and the retina of the eye. The ILM plays a role during the formation of the eye but is not required for the proper function of an adult eye. The ILM may pull at the retina and cause conditions such as macular holes, macular pucker, vitreo-macular traction syndrome, diabetic macular edema, and cystoid macular edema secondary to inflammation or venous occlusive diseases and other conditions. An epiretinal membrane (ERM) is a membrane that may form over the retina in response to damage to the retina, such as due to posterior vitreous detachment.

The ILM or ERM may need to be peeled away from the retina to prevent damage to the retina. Peeling of the ILM or ERM may also be required in preparation for surgical procedures performed on the retina. To peel the ILM or ERM, a surgical instrument is inserted through a cannula within the patient's eye globe. Forceps or a specialized scraper are typically extended from the instrument and used to raise a flap in the ILM or ERM. The flap is then grasped by the forceps and the ILM or ERM is peeled away from the retina using a circular motion. However, excess force on the forceps, however, may result in piercing of the retina.

It would, therefore, be an advancement in the art to reduce the risk of retinal damage resulting from ILM or ERM peeling.

BRIEF SUMMARY

The present disclosure relates generally to membrane-peeling tools.

In certain aspects, a membrane-peeling tool includes concentric flexible loops. For example, certain aspects provide a surgical instrument comprising a handle and an actuator mounted on the handle. An outer tube has a proximal end mounted to the handle. An outer loop extends outwardly from a distal end of the outer tube. An inner loop extends outwardly from the distal end of the outer tube and is positioned within the outer loop. The inner loop is coupled to the actuator and is configured to move relative to the outer loop responsive to movement of the actuator.

In certain aspects, a membrane-peeling tool includes independently controlled scrapers. For example, certain aspects provide an ophthalmic surgical instrument for peeling a retinal membrane including a handle. A first actuator and a second actuator are mounted on the handle. An outer tube has a proximal end mounted to the handle. An outer arm has an outer scraper secured thereto and an inner arm has an inner scraper secured thereto. The first actuator is configured to control extension of the outer arm from the outer tube and the second actuator is configured to control movement of the inner arm relative to the outer arm.

The following description and the related drawings set forth in detail certain illustrative features of one or more embodiments.

BRIEF DESCRIPTION OF THE DRAWINGS

The appended figures depict certain aspects of the one or more embodiments and are therefore not to be considered limiting of the scope of this disclosure.

To facilitate understanding, identical reference numerals have been used, where possible, to designate identical elements that are common to the drawings. It is contemplated that elements and features of one embodiment may be beneficially incorporated in other embodiments without further recitation.

DETAILED DESCRIPTION

Aspects of the present disclosure provide surgical instruments for peeling a membrane from a patient's retina. In certain aspects, a surgical instrument includes a grasping structure comprising flexible loops. In certain other aspects, a surgical instrument includes a grasping structure comprising independently actuated arcuate scrapers. Note that, herein, a distal end of a component refers to the end that is closer to a patient's body while the proximal end of the component refers to the end that is facing away from the patient's body or in proximity to, for example, the handle of the surgical instrument.

Figure 1A:
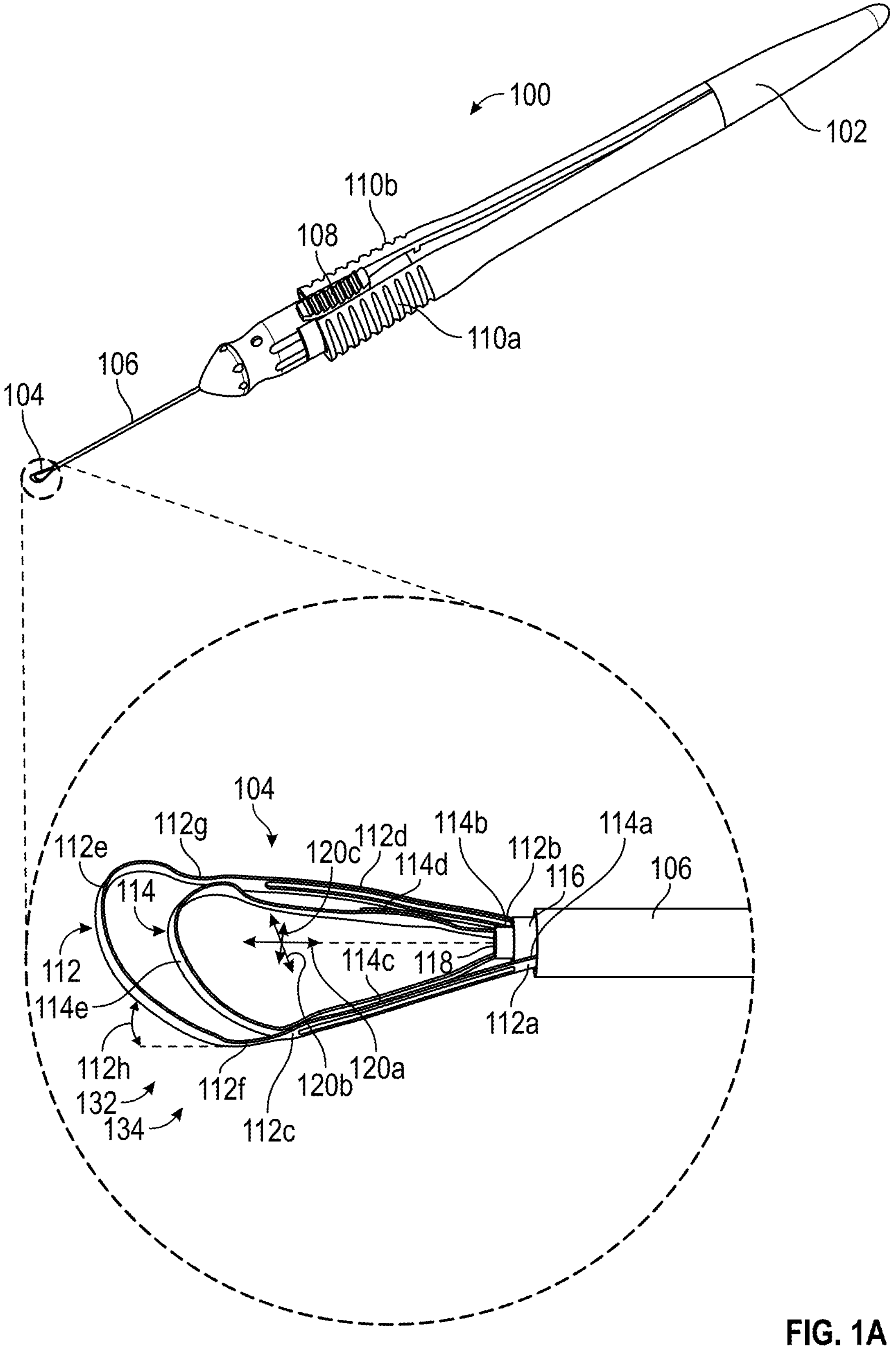
FIG. 1A is an isometric view of a surgical instrument having a grasping structure including concentric loops, in accordance with certain embodiments.
Figure 2:
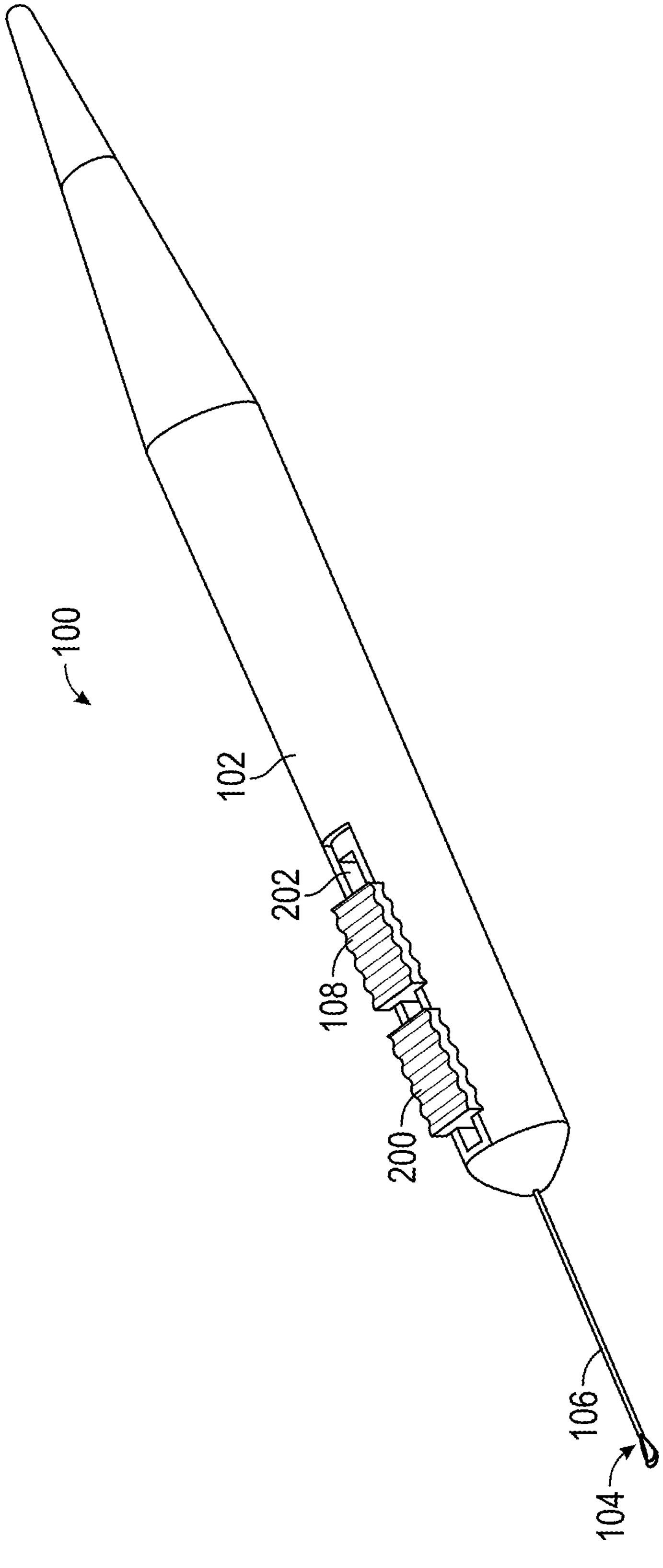
FIG. 2 is an isometric view of an alternative embodiment for actuators for controlling the grasping structure of FIGS. 1A and 1B, in accordance with certain embodiments.

FIG. 1A illustrates a surgical instrument 100, in accordance with certain embodiments described herein, including a handle 102 that is sized and contoured to be grasped by a hand of a surgeon performing an ophthalmic surgical procedure, such as peeling of a membrane from a retina of a patient's eye, including an ILM or ERM. A grasping structure 104 is extendable from a distal end of an outer tube 106, which further includes a proximal end connected to the handle 102. The handle 102 may have one or more manual control structures (e.g., actuation mechanisms) disposed thereon. In the embodiment of FIG. 1A, the manual control structures include a slider 108 and clamshell arms 110*a*, 110*b*. The manual control structures shown are only exemplary, and other manual control structures may also be used, such as a deformable basket or a second slider as shown in FIG. 2.

In FIG. 1A, the grasping structure 104 is embodied as an outer loop 112 and an inner loop 114. The outer loop 112 may be referred to as an outer grasping member of the grasping structure 104, and the inner loop 114 may be referred to as an inner grasping member of the grasping structure 104. In some embodiments, the outer tube 106 and/or the inner loop 114 are translatable relative to the outer loop 112. For example, one of the slider 108 and the clamshell arms 110*a*, 110*b* is coupled to the outer tube 106 and the other of the slider 108 and clamshell arms 110*a*, 110*b* is coupled to the inner loop 114. In use, the outer tube 106 may be extended over the outer loop 112 and inner loop 114, such as while the outer tube 106 is inserted into or withdrawn from a cannula (e.g., referred to as a trocar cannula) inserted in the patient's eye. The outer tube 106 may then be withdrawn or retracted thereby extending the outer loop 112 and inner loop 114 relative to the outer tube 106. And as discussed in greater detail below, the inner loop 114 may then be translated toward the outer loop 112 in order to grasp the membrane between the outer loop 112 and the inner loop 114.

The outer loop 112 and inner loop 114 may be made of a highly flexible material, such as nitinol (a nickel titanium alloy), spring steel, or other material. The high flexibility enables the outer loop 112 and inner loop 114 to elastically deform in order to fit within the outer tube 106 and, when extended from the outer tube 106, expand to a size that is much wider than an outer diameter of the outer tube 106, such as at least two times, four times, eight times, or at least 16 times the outer dimeter of the outer tube 106.

In the illustrated embodiments, the outer loop 112 has ends 112*a*, 112*b* fastened to an inner tube 116 slidably positioned within the outer tube 106. The inner tube 114 has ends 114*a*, 114*b* fastened to an inner rod 118 slidably positioned within the inner tube 116. The outer tube 106, inner tube 116, and inner rod 118 may be made of nitinol, stainless steel, spring steel, rigid polymer, or other material.

The outer tube 106 defines a longitudinal direction 120*a* parallel to and collinear with an axis of symmetry of the outer tube 106. The axes of symmetry of the inner tube 116 and inner rod 118 are substantially (e.g., within 0.5 mm (millimeters)) collinear with the longitudinal direction 120*a* and substantially (e.g., within 5 degrees of) parallel to the longitudinal direction 120*a*. A transverse direction 120*b* may also be defined as perpendicular to the longitudinal direction 120*a* such that the ends 112*a*, 112*b* of the outer loop 112 are offset from one another along the transverse direction 120*b* and the ends 114*a*, 114*b* of the inner loop 114 are offset from one another along the transverse direction 120*b*. A vertical direction 120*c* may be defined as perpendicular to the longitudinal direction 120*a* and the transverse direction 120*b*.

The outer loop 112 may include straight portions 112*c*, 112*d* extending from the ends 112*a*, 112*b*, respectively. The straight portions 112*c*, 112*d* may be intersected by a plane containing the longitudinal direction 120*a* and transverse direction 120*b* ("the longitudinal-transverse plane"). The straight portions 112*c*, 112*d* may diverge from one another in the longitudinal transverse plane, i.e., flare outwardly from one another with distance from the distal end of the outer tube 106. As used herein, "straight" may be understood as having a radius of curvature in the longitudinal-transverse plane of greater than 1 cm (centimeter). As used herein, the longitudinal transverse plane comprises the plane containing both the longitudinal direction 120*a* and transverse direction 120*b*.

The straight portions 112*c*, 112*d* may be connected to one another by a rounded end portion 112*e*. The rounded end portion 112*e* may be either (a) formed to hold a rounded shape absent an external force or (b) the result of bending of the outer loop 112 and securement of the ends 112*a*, 112*b* to the inner tube 116. The rounded shape may be circular, elliptical, or any arbitrary rounded shape.

Rounded end portion 112*e* may be secured to the straight portions 112*c*, 112*d* by flexible portions 112*f*, 112*g*. The flexible portions 112*f*, 112*g* have a reduced height (e.g., perpendicular to the longitudinal-transverse plane) and/or thickness (e.g., parallel to the longitudinal-transverse plane) relative to one or both of the rounded end portion 112*e* and the straight portions 112*c*, 112*d*. For example, in the illustrated embodiment, the thickness of the flexible portions 112*f*, 112*g* is substantially (e.g., within 10 percent of) the same as that of the straight portions 112*c*, 112*d* and the rounded end portion 112*e* whereas the height of the flexible portions 112*f*, 112*g* is between 0.25 and 0.75 times or between 0.4 and 0.6 times the height of the straight portions 112*c*, 112*d* and the rounded end portion 112*e*. As is apparent in FIG. 1A, there may be a smooth transition between the reduced cross-section of the flexible portions 112*f*, 112*g* and the cross-sections of the rounded end portion 112*e* and straight portions 112*c*, 112*d*.

The flexible portions 112*f*, 112*g* may function as a live hinge facilitating rotation of the rounded end portion 112*e* relative to the straight portions 112*c*, 112*d*. In other embodiments, there are no discrete flexible portions. In such embodiments, some or all of the expanse between the rounded end portion 112*e* and the ends 112*a*, 112*b* provides flexibility.

It is desirable that a lower surface 132 of the rounded end portion 112*e* be relatively parallel to the retina to reduce risk of puncture. In response to pressure exerted on the rounded end portion 112*e* by the membrane during use, the rounded end portion 112*e* will rotate until the lower surface 132 of the rounded end portion 112*e* is resting on the membrane, thereby increasing the surface area in contact with the membrane and reducing risk of puncture. The cross-sectional shape of the rounded end portion 112*e* may have a height (e.g., perpendicular to the longitudinal-transverse plane) that is much greater than the thickness (e.g., parallel to the longitudinal-transverse plane) such that the rounded end portion 112*e* does not substantially flex in a plane parallel to the longitudinal direction 120*a* and the vertical direction 120*c* ("the longitudinal-vertical plane"), such as height that is at least two, four, eight, or a greater multiple of the thickness. This may facilitate the lower surface 132 of the rounded end portion 112*e* providing a broad surface that resists penetrating the retina.

In some implementations, the flexible portions 112*f*, 112*g* may further define a bend in the absence of any deforming force such that the rounded end portion 112*e* defines an angle 112*h* relative to the longitudinal-transverse plane and is raised above the longitudinal-transverse plane. The angle 112*h* may further encourage the rounded end portion 112*e* to rotate when pushed against the membrane rather than puncturing the membrane and possibly the retina.

The inner loop 114 may include straight portions 114*c*, 114*d* extending from the ends 114*a*, 114*b*, respectively. The straight portions 114*c*, 114*d* may be intersected by the longitudinal-transverse plane. The straight portions 114*c*, 114*d* may diverge from one another in the longitudinal transverse plane, i.e., flare outwardly from one another with distance from the distal end of the outer tube 106.

The straight portions 114*c*, 114*d* may be connected to one another by a rounded end portion 114*e*. The rounded end portion 114*e* may be either (a) formed to hold a rounded shape absent an external force or (b) the result of bending of the inner loop 114 and securement of the ends 114*a*, 114*b* to the inner tube 116. The rounded end portion 114*e* may be angled relative to the longitudinal-transverse plane by the same angle 112*h* or a different angle. Absent a deforming force, the rounded end portion 114*e* may have an outer surface having a size in a plane of curvature (e.g., the longitudinal-transverse plane or a plane oriented at the angle 112*h* relative to the longitudinal-transverse plane) that is substantially equal to a size of the outer surface of the rounded end portion 112*e*, a size of the inner surface of the rounded end portion 112*e*, or smaller than the inner diameter of the rounded end portion 112*e*. Flexibility of the outer loop 112 and inner loop 114 enable the outer loop 112 and inner loop 114 to nest regardless of size when undeformed.

In the illustrated implementation, the straight portions 114*c*, 114*d* may have a reduced height and/or thickness relative to the straight portions 112*c*, 112*d* and the rounded end portion 114*e* such that the inner loop 114 is more flexible than the outer loop 112 and such that discrete flexible portions analogous to the flexible portions 112*f*, 112*g* are not formed between the straight portions 114*c*, 114*d* and the rounded end portion 114*e*. However, in other implementations, flexible portions are used in a like manner. As discussed in greater detail below, the outer loop 112 may be used to raise a flap in the membrane, which may require a degree of pressure to be exerted on the membrane. In contrast, the inner loop 114 need only press the flap against the outer loop 112. Accordingly, the inner loop 114 may be made more flexible in order to reduce risk of puncture while still being sufficiently rigid to press the flap against the outer loop 112.

Figure 1B:
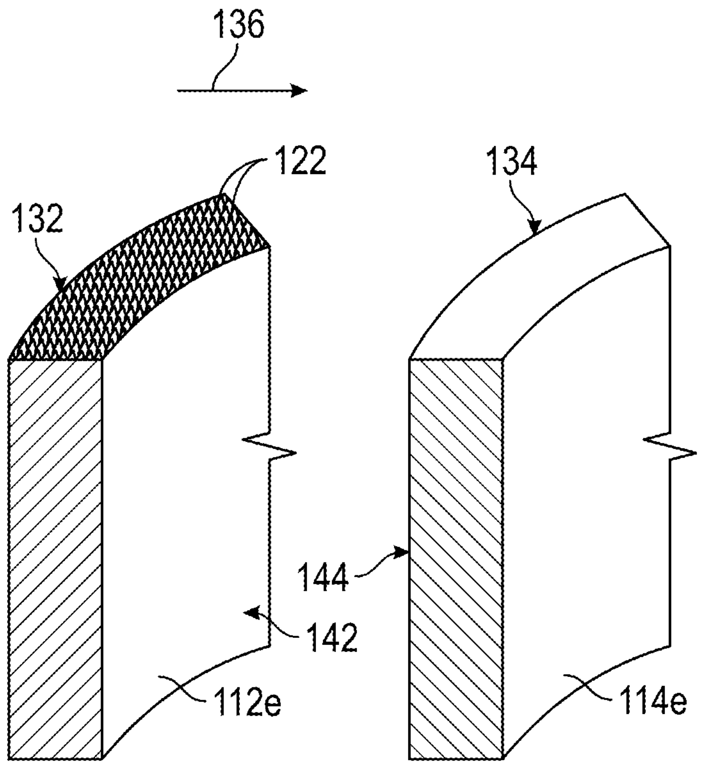
FIG. 1B is a cutaway view of the concentric loops in FIG. 1A, in accordance with certain embodiments.

Referring to FIG. 1B, one or both of the lower surfaces 132 and 134 of the rounded end portion 112*e* and rounded end portion 114*e*, respectively, may have structures formed thereon to facilitate gripping of the membrane. For example, the lower surfaces 132, 134 may have barbs 122 formed thereon. For the rounded end portion 112*e*, the barbs 122 may point toward the rounded end portion 114*e*, as indicated by arrow 136. Stated differently, the barbs 122 on the rounded end portion 114*e* are oriented such that movement of the rounded end portion 112*e* relative to the membrane will be resisted more for relative movement of the rounded end portion 112*e* toward the rounded end portion 114*e* than for relative movement away from the rounded end portion 114*e*. In this manner, the barbs 122 enhance the ability of the rounded end portion 112*e* to pull the membrane and raise a flap between the rounded end portions 112*e*, 114*e*. The barbs 122 may be tapered such that the resistance of the membrane to penetration by the barbs 122 increases with depth. This reduces the risk of the barbs 122 passing completely through the membrane. In some applications, the tapered shape of the barbs 122 prevent the lower surface 132 of the rounded end portion 112*e* from actually contacting the membrane during use.

In the embodiments of FIG. 1B, the rounded end portion 114*e* lacks barbs on the lower surface 134. In other embodiments, barbs 122 are included on the lower surface 134 of the rounded end portion 114*e*. In such embodiments, the barbs 122 may point in the opposite direction from the barbs 122 on the rounded end portion 112*e* such that the barbs 122 improve the ability of the rounded end portion 114*e* to push the membrane toward the rounded end portion 112*e*. Again, in other embodiments, no barbs are formed on the lower surface 134 of the rounded end portion 114*e* such that the rounded end portion 114*e* is primarily or exclusively responsible for grasping the flap.

In some embodiments, an inner surface 142 of the rounded end portion 112*e* (surface facing the rounded end portion 114*e*) and an outer surface 144 of the rounded end portion 114*e* (surface facing the rounded end portion 112*e*) are textured, barbed, coated with a gripping material (e.g., silicone) in order to resist slipping of the flap when grasped between the rounded end portion 112*e* and rounded end portion 114*e*.

Referring to FIG. 2, various actuation mechanisms may be used to manually control translation of the outer tube 106 and the inner rod 118. In some embodiments, the clamshell arms 110*a*, 110*b* may be replaced with a second slider 200 that is slidably mounted to the handle 102. In the illustrated embodiment, the sliders 108, 200 both slide within a common slot 202 defined by the handle 102. Accordingly, one slider 108 may control actuation of the outer tube 106, and the other slider 200 may control actuation of the inner loop 114, or vice versa.

Figure 3:
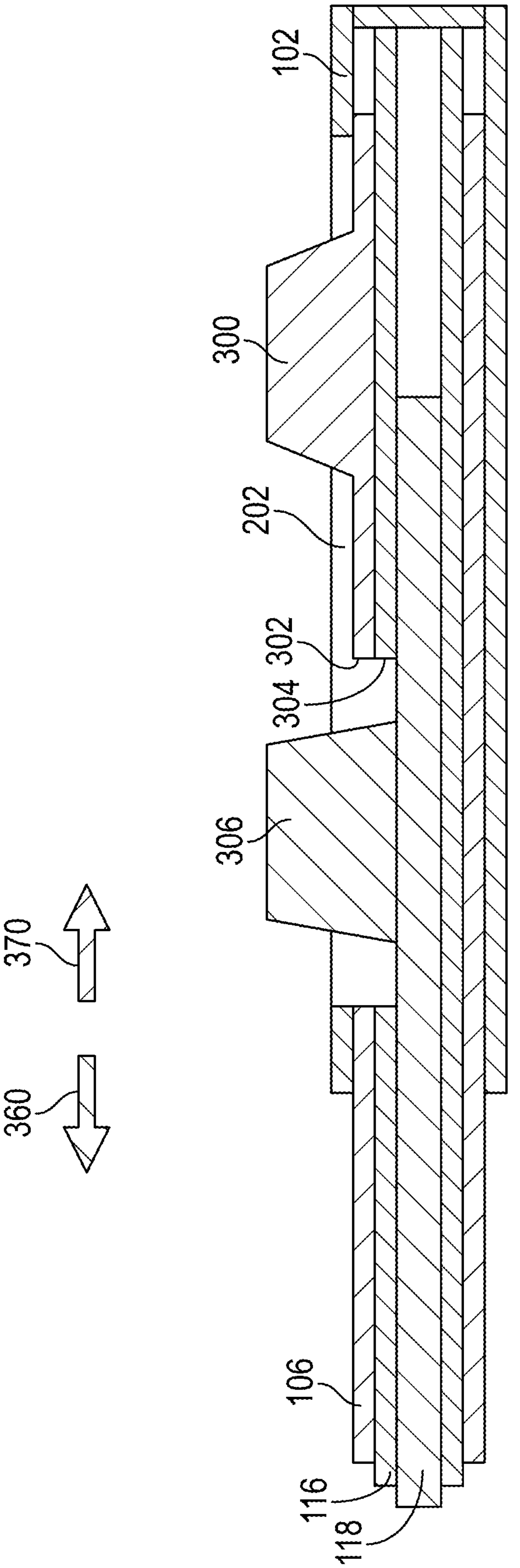
FIG. 3 is a cross-sectional view illustrating a mechanism for actuating the concentric loops of the grasping structure of FIGS. 1A and 1B, in accordance with certain embodiments.

FIG. 3 illustrates an example mechanism for coupling the slider 108 and clamshell arms 110*a*, 110*b* to the outer tube 106 and inner rod 118 or coupling the slider 108 and slider 200 to the outer tube 106 and the inner rod 118. The illustrated mechanism is only exemplary and shows an example relative movement of components. However, the actual size and relative position of components may vary. For purposes of FIG. 3, "first actuator" and "second actuator" refer to the slider 108 and clamshell arms 110*a*, 110*b*. The "first actuator" and "second actuator" may also refer to the slider 108 and the slider 200, or vice versa.

In the illustrated embodiment, the inner tube 116 is fixed relative to the handle 102. The outer tube 106 is slidable relative to the handle 102 and has a mounting structure 300 fastened thereto. The mounting structure 300 is also slidable relative to the handle 102 and is coupled to the first actuator. The outer tube 106 defines a slot 302 and the inner tube 116 defines a slot 304. A mounting structure 306 is fastened to the inner rod 118 and slidable within the slots 302, 304. The mounting structure 306 is coupled to the second actuator.

Various alternatives to the illustrated configuration are possible. For example, the inner rod 118 may be fixed relative to the handle 102 and the mounting structure 306 may be fastened to the inner tube 116, which may be slidable relative to the handle 102.

In use, the first actuator may be moved in a first direction to move the outer tube 106 outwardly from the handle 102 and over the outer loop 112 and the inner loop 114. The first actuator may be moved in a second direction opposite the first direction to move the outer tube 106 inwardly thereby extending the outer loop 112 and the inner loop 114 from the distal end of the outer tube 106.

The first direction for a slider 108 or slider 200 may be defined as movement 360 toward the distal end of the outer tube 106 and the second direction may be a movement 370 of the slider 108 or slider 200 away from the distal end of the outer tube 106. For the basket 110, the first direction may be defined as expansion of the clamshell arms 110*a*, 110*b*, i.e., releasing of pressure urging the clamshell arms 110*a*, 110*b*, and the second direction may be defined as pressing the clamshell arms 110*a*, 110*b* toward one another. The second actuator may be moved in the first direction to move the inner loop 114 toward the outer loop 112 in order to grasp a flap of a membrane. The second actuator may be moved in the second direction to move the inner loop 114 away from the outer loop 112. Where the outer loop 112 and inner tube 116 are actuated by the second actuator, the second actuator may be moved in the first direction to move the outer loop 112 away from the inner loop and moved in the second direction to move the outer loop 112 toward the inner loop 114 in order to grasp a flap of a membrane.

Figure 4A:
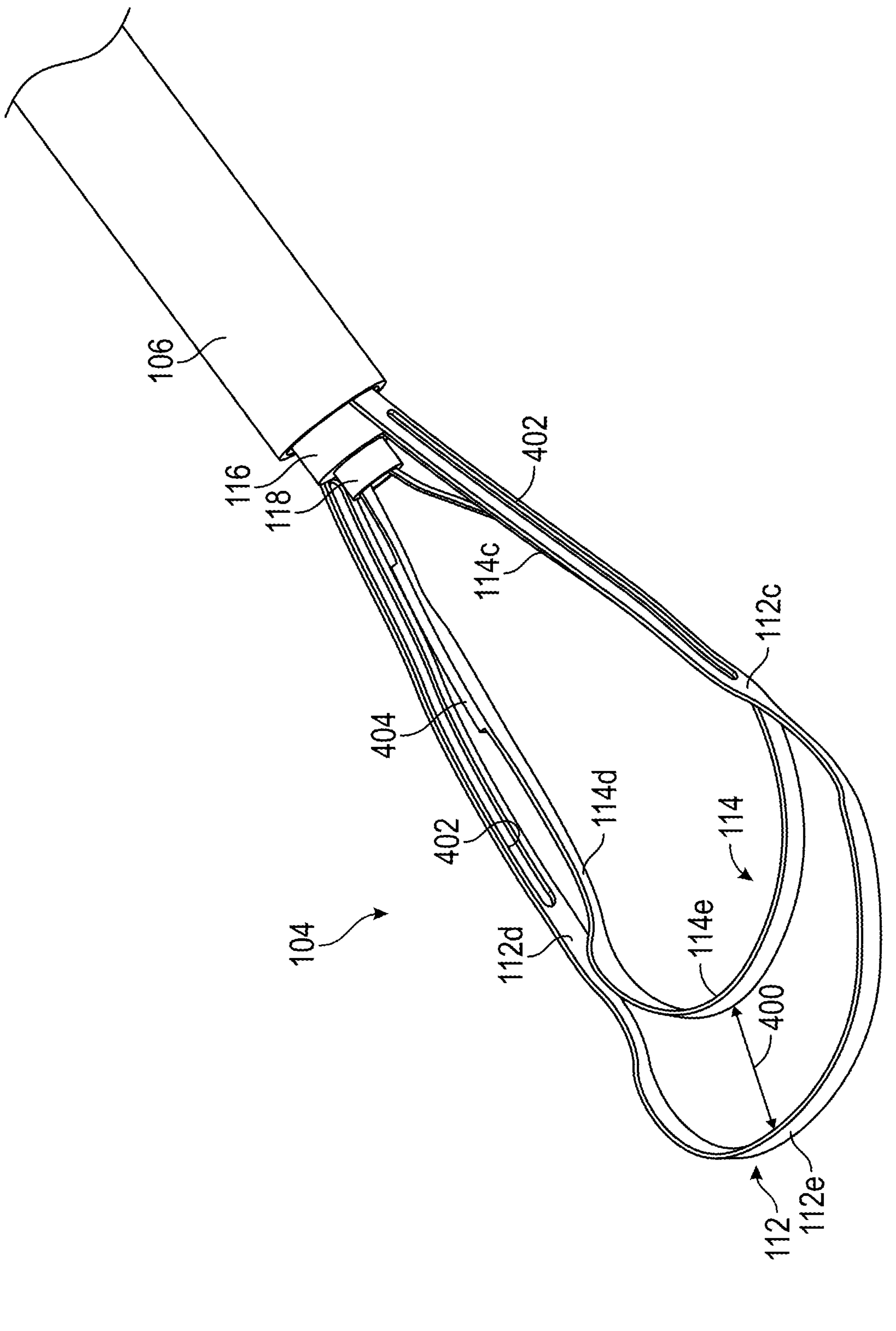
FIG. 4A is an isometric view showing the concentric loops of the grasping structure of FIGS. 1A and 1B in an open configuration, in accordance with certain embodiments.
Figure 4B:
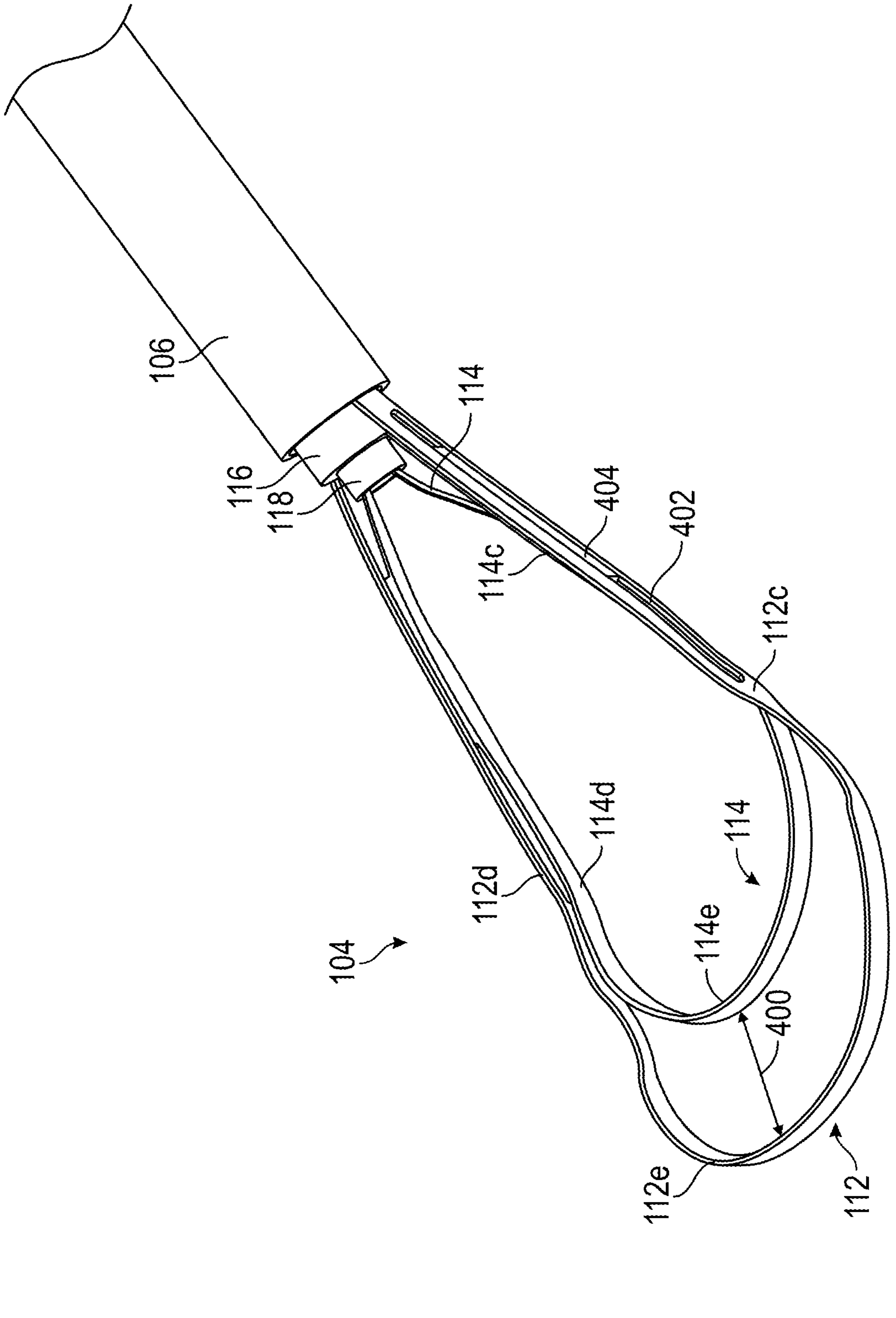
FIG. 4B is an isometric view showing the concentric loops of the grasping structure of FIGS. 1A and 1B in an open configuration with an alignment structure of an inner loop engaged with an outer loop, in accordance with certain embodiments.

Referring now to FIG. 4A, in preparation for raising a flap, the outer loop 112 and the inner loop 114 may be positioned in the illustrated open configuration with a gap 400 between the rounded end portion 112*e* and the rounded end portion 114*e* that is many times greater than the thickness of the membrane, e.g. at least 10, 100, or 1000 times the thickness of the membrane. Referring to FIG. 4B, in some embodiments, the straight portions 112*c*, 112*d* define slots 402 and the straight portions 114*c*, 114*d* define protrusions 404 that can insert within the slots 402. The protrusions 404 are slidable within the slots 402 for at least part of the range of motion of the inner loop 114, e.g., for some range of motion beginning with the rounded end portion 114*e* pressed against the rounded end portion 112*e*. The protrusions 404 may be freely insertable within the slots 402 or may resist removal (e.g., a slightly enlarged distal end). The positions of the slots 402 and protrusions 404 may be reversed: slots 402 formed on the straight portions 114*c*, 114*d* and protrusions 404 formed on the straight portions 112*c*, 112*c*.

The engagement of the slots 402 with the protrusions 404 may function to maintain the loops aligned with one another during use. For example, this may prevent the inner loop 114 from being positioned above the outer loop 112 and failing to engage the flap of the membrane. However, using flexibility of the outer loop 112 and inner loop 114, both loops may be pressed against the membrane ensuring that the inner loop 114 will engage the flap when moved toward the outer loop 112. Accordingly, the slots 402 and protrusions 404 may be omitted in some embodiments.

Figure 5A:
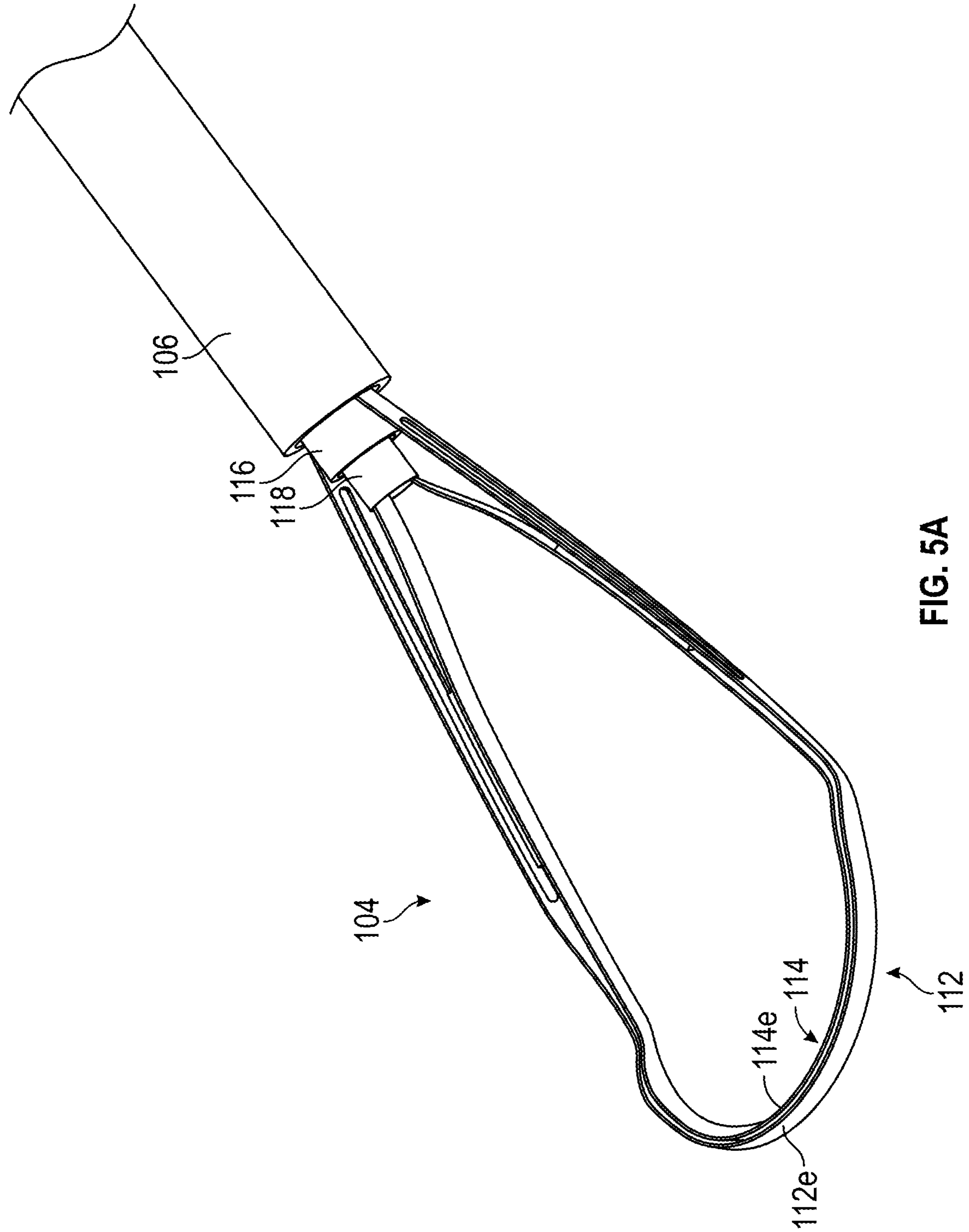
FIG. 5A is an isometric view showing the concentric loops of the grasping structure of FIGS. 1A and 1B in a closed configuration, in accordance with certain embodiments.

Referring to FIG. 5A, the surgeon may translate the second actuator (e.g., compress the clamshell arms 110*a*, 110*b* or translate the slider 200) toward the distal end of the handle 102 (toward the outer tube 106) in order to urge the inner loop 114 toward the outer loop 112 to achieve the illustrated closed configuration. As is apparent, the rounded end portion 114*e* will nest within the rounded end portion 112*e* thereby firmly grasping a flap raised by the rounded end portion 112*e*. The separation between the rounded end portion 114*e* and the rounded end portion 112*e* may be less than or equal to four, three, or two times the thickness of the membrane when in the closed configuration.

Figure 5B:
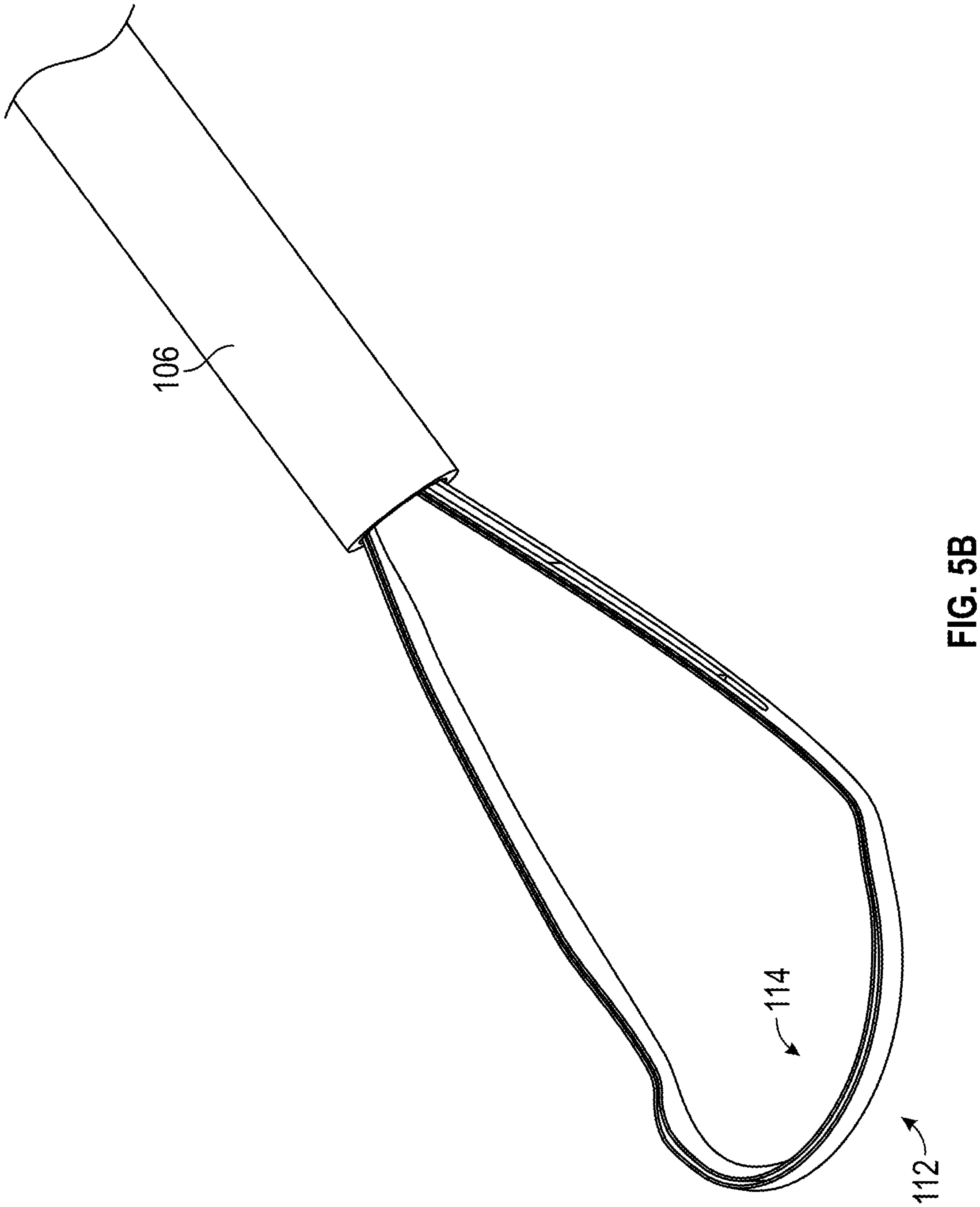
FIG. 5B is an isometric view showing an outer tube extended partially over the concentric loops of the grasping structure of FIGS. 1A and 1B, in accordance with certain embodiments.

Referring to FIG. 5B, the outer tube 106 may be extended partially or completely over the outer loop 112 and inner loop 114 at any point during use of the surgical instrument 100. The stiffness of the outer loop 112 and inner loop 114 may be increased by extending the outer tube 106 and reducing the portions of the outer loop 112 and inner loop 114 that are positioned outwardly from the outer tube 106. Likewise, where more flexibility is desired, the outer tube 106 may be withdrawn to the point that more, potentially the entirety, of the outer loop 112 and inner loop 114 are exposed.

As noted above, in preparation for insertion of the outer tube 106 through the cannula, the outer tube 106 may be extended until either (a) the outer loop 112 and inner loop 114 are located completely within the outer tube 106 or (b) the parts of the outer loop 112 and inner loop 114 extending outwardly from the outer tube 106 are small enough to fit through the cannula (e.g., equal to or smaller than the outer diameter of the outer tube 106).

Figure 6A:
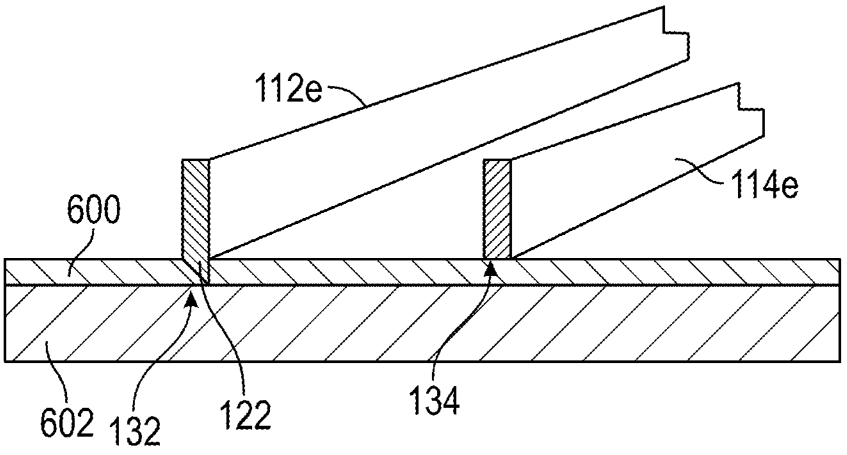
FIGS. 6A to 6C are cross-sectional views showing the peeling of an ILM using the grasping structure of FIGS. 1A and 1B, in accordance with certain embodiments.
Figure 6B:
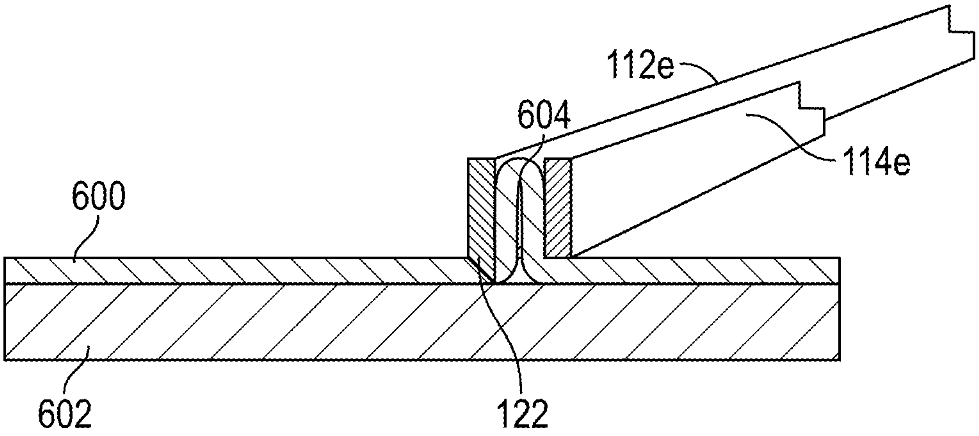
Figure 6C:
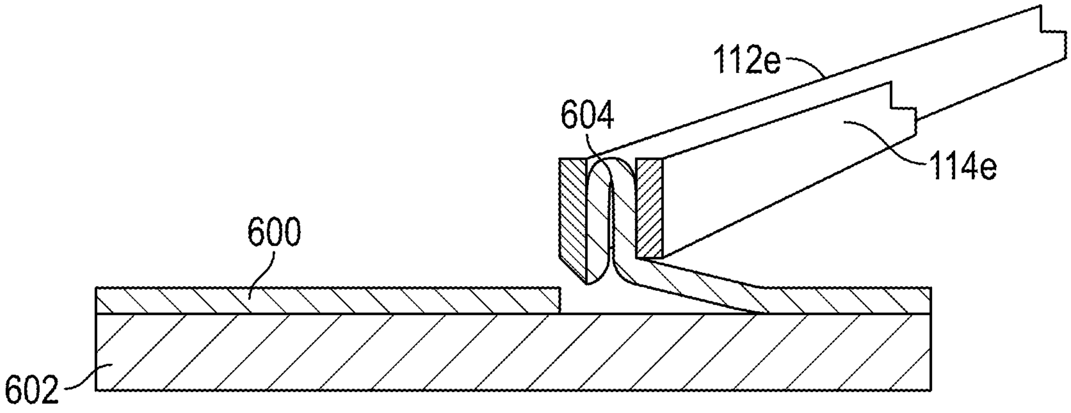
Figure 7:
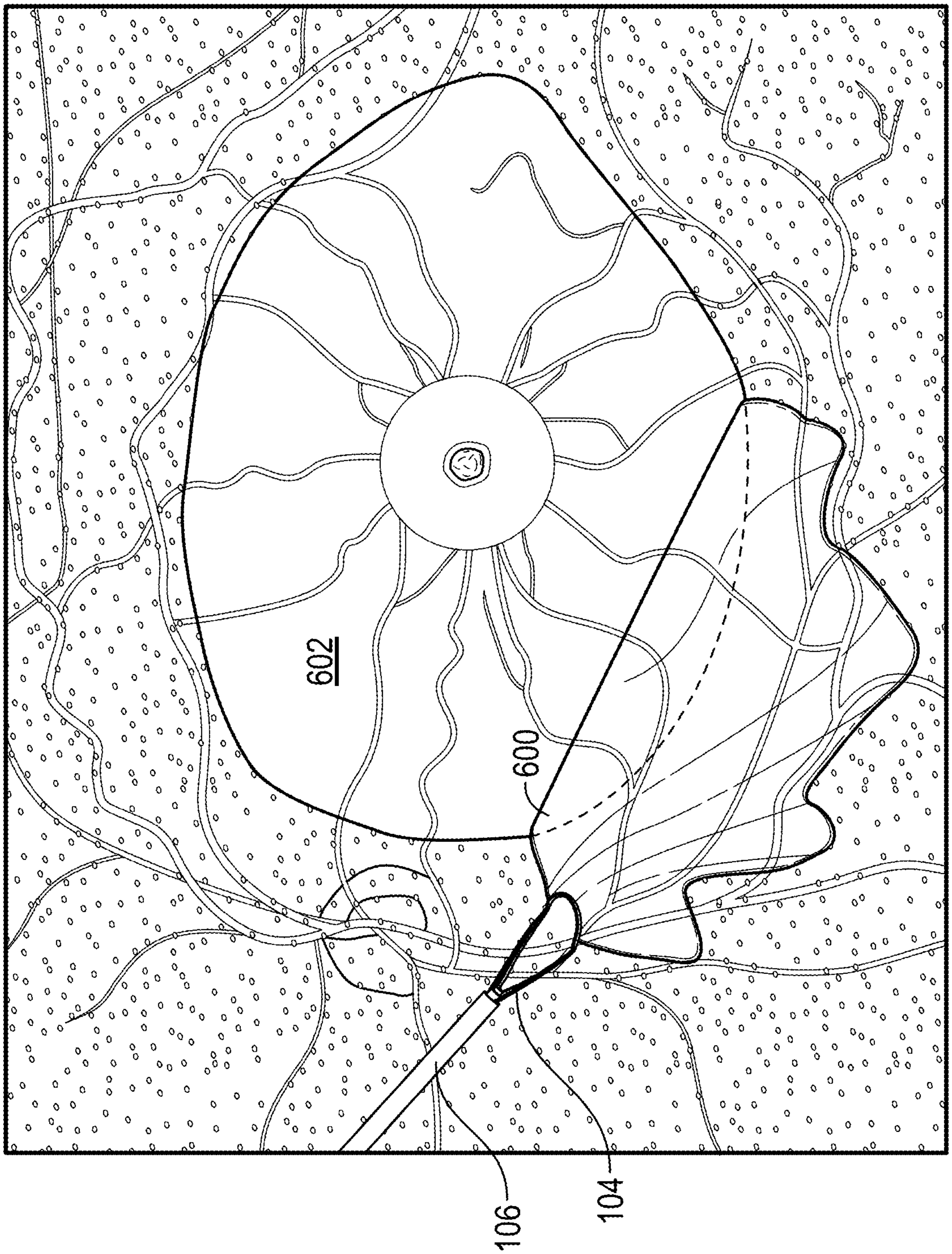
FIG. 7 is an isometric view showing an ILM being peeled using the grasping structure of FIGS. 1A and 1B, in accordance with certain embodiments.

Referring now to FIG. 6A, during use, lower surfaces 132, 134 of the rounded end portions 112*e*, 114*e* are pressed against the membrane 600 (e.g., ILM or ERM) positioned over the retina 602. As shown, the barbs 122 may at least partially penetrate the ILM. The extent of the barbs 122 below the lower surface of the rounded end portions 112*e*, 114*e* may be less than the thickness of the ILM, such as less than 2 to 10 microns. For example, the barbs 122 may have a length outward from the lower surface of between 0.8 and 8 microns. Referring to FIG. 6B, a flap 604 may be raised by drawing the rounded end portion 112*e* across the membrane 600 and the rounded end portion 114*e* may be urged toward the rounded end portion 112*e* in order to grasp the flap 604 firmly. Referring to FIG. 6C, the surgeon may then lift the surgical instrument 100 in order to tear the membrane 600. Referring to FIG. 7, the surgeon may move the grasping structure 104 in a circular motion to peel a portion of the membrane 600 away from the retina 602.

Various alternatives to the illustrated method of use of the surgical instrument 100 are possible. For example, the inner loop 114 may be fixed relative to the handle 102 as described above and the outer loop 112 may be actuated. The outer loop 112 may therefore be actuated to move the rounded end portion 112*e* toward the rounded end portion 114*e* and thereby both raise the flap 604 and grasp the flap 604 between the rounded end portion 112*e* and the rounded end portion 114*e* in a single motion. In other methods of use, the rounded end portion 112*e* is drawn across the membrane 600 in the direction of the rounded end portion 114*e* to raise the flap 604 without decreasing the distance between the rounded end portion 112*e* and the rounded end portion 114*e*. The rounded end portion 112*e* is then drawn toward the rounded end portion 114*e* using the second actuator, which will further raise the flap 604 and grasp the flap 604 between the rounded end portion 112*e* and the rounded end portion 114*e*.

Figure 8A:
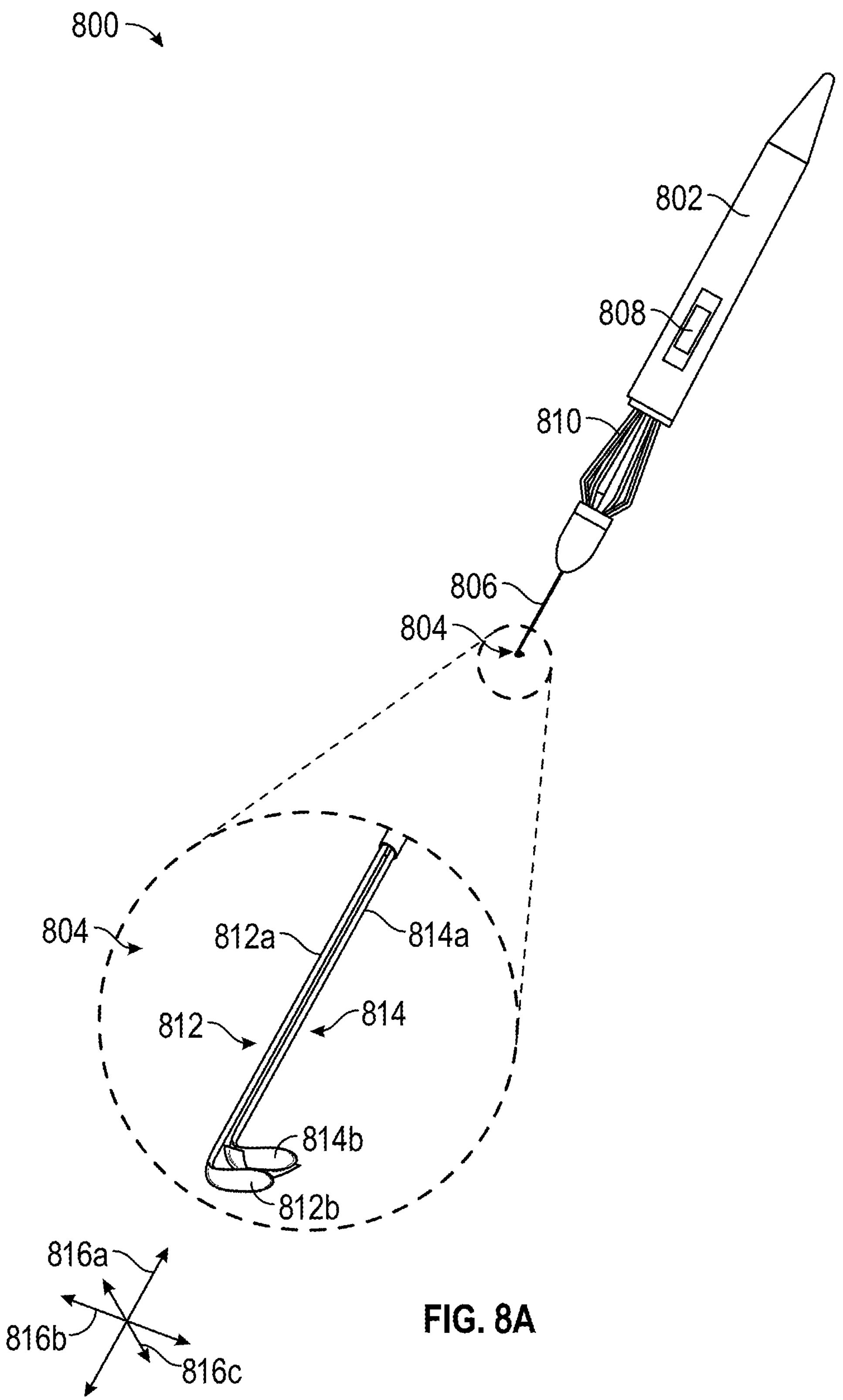
FIG. 8A is an isometric view of a surgical instrument having another grasping structure including independently actuated arcuate scrapers, in accordance with certain embodiments.

FIG. 8A illustrates another ophthalmic surgical instrument 800, in accordance with certain embodiments, including a handle 802 that is sized and contoured to be grasped by a hand of a surgeon performing an ophthalmic surgical procedure such as peeling of a membrane from a retina of a patient's eye, such as an ILM or ERM. A grasping structure 804 is extendable from a distal end of an outer tube 806 connected to the handle 802. This proximal end of the outer tube 806 is connected to the handle 802. The handle 802 may have one or more manual control structures mounted thereto for manual actuation of the grasping structure 804. In the embodiment of FIG. 8A, the manual control structures include a slider 808 and a deformable basket 810. The manual control structures shown are exemplary only and other manual control structures and/or combinations of manual control structures may also be used (e.g., see FIG. 9).

The grasping structure 804 in FIG. 8A is embodied as outer arm 812 and an inner arm 814. The outer arm 812 may be referred to as an outer grasping member of the grasping structure 804, and the inner arm 814 may be referred to as an inner grasping member of the grasping structure 804. The outer tube 806 may define a longitudinal direction 816*a* that is parallel to the axis of symmetry of the outer tube 806. The outer arm 812 and inner arm 814 may include straight portions 812*a*, 814*a* that extend substantially (e.g., within 5-15 degrees of) parallel to the longitudinal direction 816*a*. The outer arm 812 and inner arm 814 are offset from one another along substantially (e.g., within 5 degrees of) parallel to a transverse direction 816*b* that is defined as perpendicular to the longitudinal direction 816*a*. A vertical direction 816*c* may be defined as perpendicular to the longitudinal direction 816*a* and the transverse direction 816*b*. The straight portions 812*a*, 814*a* may be implemented as hollow cylindrical tubes, solid cylindrical rods, or have some other solid or hollow cross-sectional shape in a plane perpendicular to the longitudinal direction 816*a*.

The straight portions 812*a*, 814*a* have a scraper 812*b*, 814*b* secured to the distal ends thereof. The scrapers 812*b*, 814*b* extend generally (e.g., within 15 degrees of) perpendicular to the longitudinal direction 816*a* and outwardly from the straight portions 812*a*, 814*a*. The scrapers 812*b*, 814*b* may each have an arcuate shape, such as an elongated spoon shape. The scrapers 812*b*, 814*b* may have an arcuate shape in a plane substantially (e.g., within 15 degrees of) perpendicular to the longitudinal direction 816*a* and the transverse direction 816*b*. The scrapers 812*b*, 814*b* may have an arcuate shape in a plane substantially (e.g., within 15 degrees of) perpendicular to the longitudinal direction 816*a* and the vertical direction 816*c*. The scrapers 812*b*, 814*b* may have an ellipsoid or any other three-dimensional curved shape. The scrapers 812*b*, 814*b* may have arcuate shapes on both inner (facing the outer tube 806) and outer (facing away from the outer tube 806) surfaces. The scrapers 812*b*, 814*b* may at least partially nest: part of the outer surface of the scraper 814*b*, which is convex, is positioned within a cavity defined by the inner surface of the scraper 812*b*, which is concave. The scrapers 812*b*, 814*b* may be identical, within manufacturing tolerances, or the scraper 812*b* may be made larger to better receive the scraper 814*b* when nested.

Figure 8B:
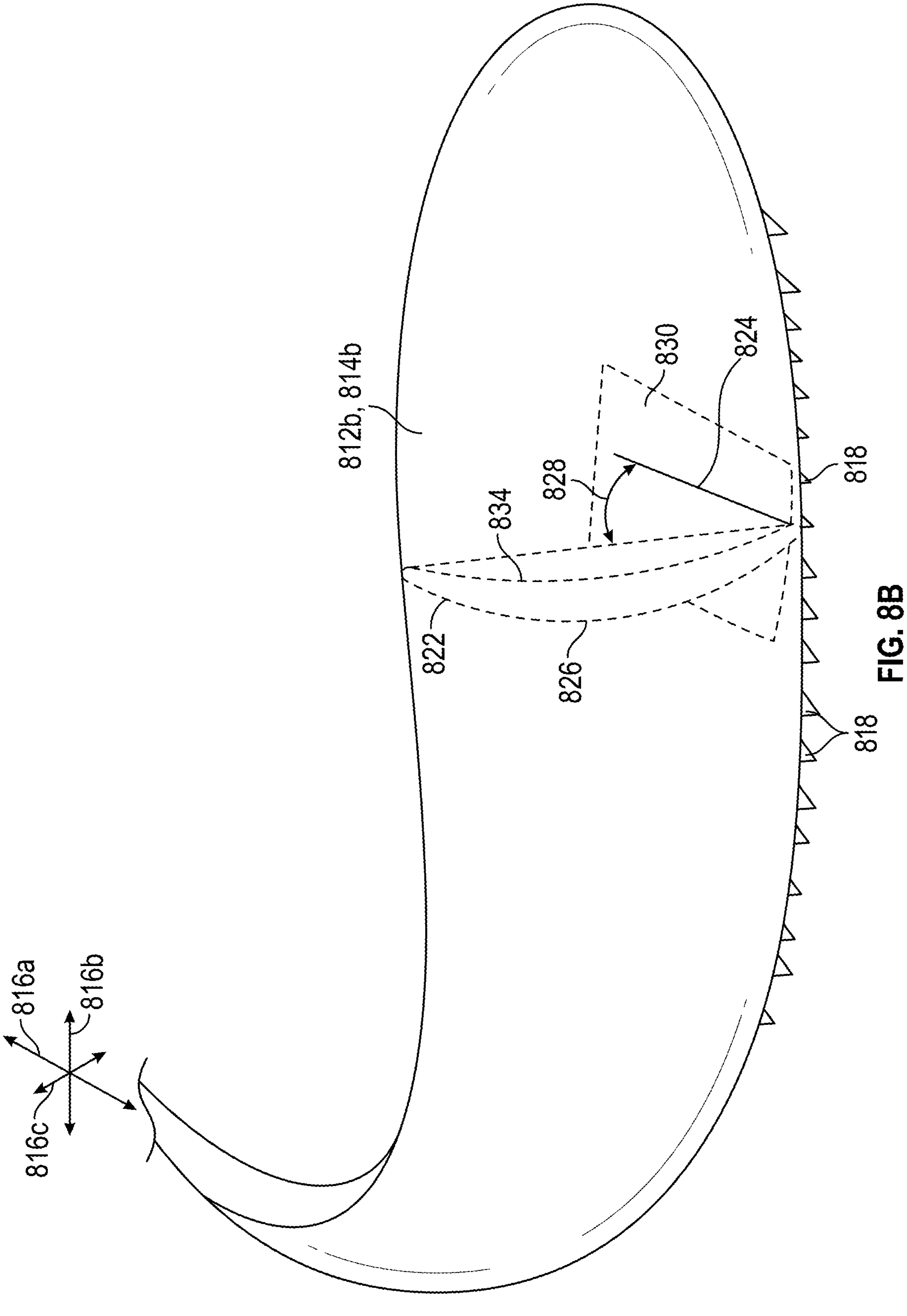
FIG. 8B is an isometric view of an arcuate scraper in FIG. 8A having barbs on a lower edge thereof, in accordance with certain embodiments.

Referring to FIG. 8B, one or both of the scrapers 812*b*, 814*b* may include barbs 818. The barbs 818 of the scraper 812*b* may be oriented such that the barbs 818 will catch the membrane more effectively when the scraper 812*b* is moved in the direction in which the concave surface of the scraper 812*b* is facing than when moved across the membrane in the opposite direction. The barbs 818 of the scraper 814*b* may point in the opposite direction. The barbs 818 of the scraper 814*b* will catch the membrane less effectively when the scraper 814*b* is moved in the direction in which the concave surface of the scraper 814*b* is facing than when moved across the membrane in the opposite direction.

The barbs 818 extend outwardly from the lower edge of the scrapers 812*b*, 814*b* a length less than the thickness of the membrane being peeled. For example, the membrane may have a thickness of 4 microns. The barbs 818 may have a length outward from the lower edges of the scrapers 812*b*, 814*b* of between 1 and 3 microns.

The inner arm 814 and outer arm 812 may be made of a highly flexible material, such as nitinol (a nickel titanium alloy), spring steel, polymeric material, or other material. The high flexibility enables the scrapers 812*b*, 814*b* to elastically deform in order to fit within the outer tube 806 and, when extended from the outer tube 806, recoil outwardly in the transverse direction 816*b* further than the outer diameter of the outer tube 806. For example, the scrapers 812*b*, 814*b* may extend outwardly from the longitudinal direction 816*a* in the transverse direction 816*b* at least one times, two times, four times, eight times, or some other multiple of the diameter of the outer tube. As shown in FIG. 8A, in some implementations, the scrapers 812*b*, 814*b* both extend outwardly from the outer tube 806 on only one side of a plane defined by the longitudinal direction 816*a* and vertical direction 816*c*.

FIG. 8B further illustrates the shape of the scrapers 812*b*, 814*b*. As shown by the cross-sectional shape 822, the scrapers 812*b*, 814*b* have a concave inner surface 834 and a convex outer surface 826. The cross-sectional shape 822 may be defined with respect to a section plane parallel to the longitudinal direction 816*a* and the vertical direction 816*c*. The concave inner surface 834 of the scraper 812*b* and the convex outer surface 826 of the scraper 814*b* may be textured to facilitate gripping. The texturing may be any treatment or pattern that improves griping of the membrane, such as an increase in roughness due to a process such as sanding or grinding, formation of a regular pattern of peaks and valleys, an array of barbs, or other texturing.

A line 824 may be defined as tangent to the scrapers 812*b*, 814*b* at two points above and below the concave inner surface 834. The line 824 may be used to understand the orientation of the scrapers 812*b*, 814*b*. The line 824 defines an angle 828 with respect to a plane 830 that is parallel to the longitudinal direction 816*a* and the transverse direction 816*b*. The outer tube 806 may be inserted within a trocar cannula that is offset from the pupil of the eye of the patient whereas the membrane to be peeled may be located directly behind the pupil. The longitudinal direction 816*a*, may therefore be at a non-parallel angle with respect to a normal vector of the membrane at a point of contact with each scraper 812*b*, 814*b*. The angle 828 may be selected such that, in use, the line 824 is substantially (e.g., within 15 degrees of) parallel to the normal vector of the membrane at a point of contact between the scraper 812*b*, 814*b* and the membrane at the section plane 822. For example, the angle 828 may be between 75 and 105 degrees. This relationship between the line 824 and the normal vector and the point of contact may be present along a major portion, such as at least 80 percent, of the extent of the scraper 812*b*, 814*b* in the transverse direction 816*b*.

Figure 9:
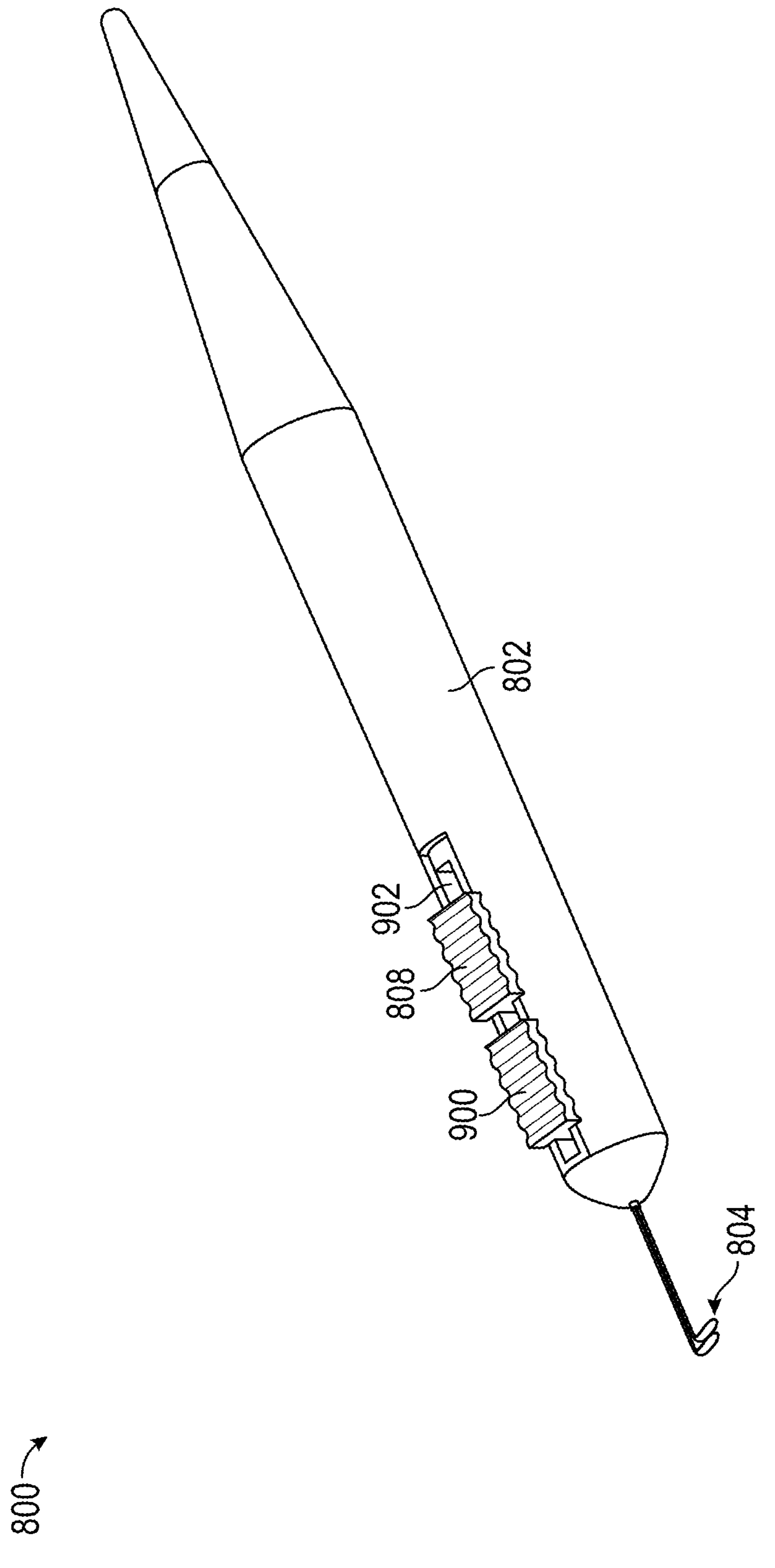
FIG. 9 is an isometric view of an alternative embodiment for actuators for controlling the grasping structure of FIGS. 8A and 8B, in accordance with certain embodiments.

Referring to FIG. 9, various manual actuation mechanisms and/or control structures may be used to control translation of one or both of the arms 812, 814. In some embodiments, the deformable basket 810 may be replaced with a second slider 900 that is slidably mounted to the handle 802. In the illustrated embodiment, the sliders 808, 900 both slide within a common slot 902 defined by the handle 802. The slider 808, deformable basket 810, and slider 900 are exemplary only. Any actuation mechanism or structure known in the art, such as a button, may be used to control the movement of one or both arms 812, 814.

Figure 10:
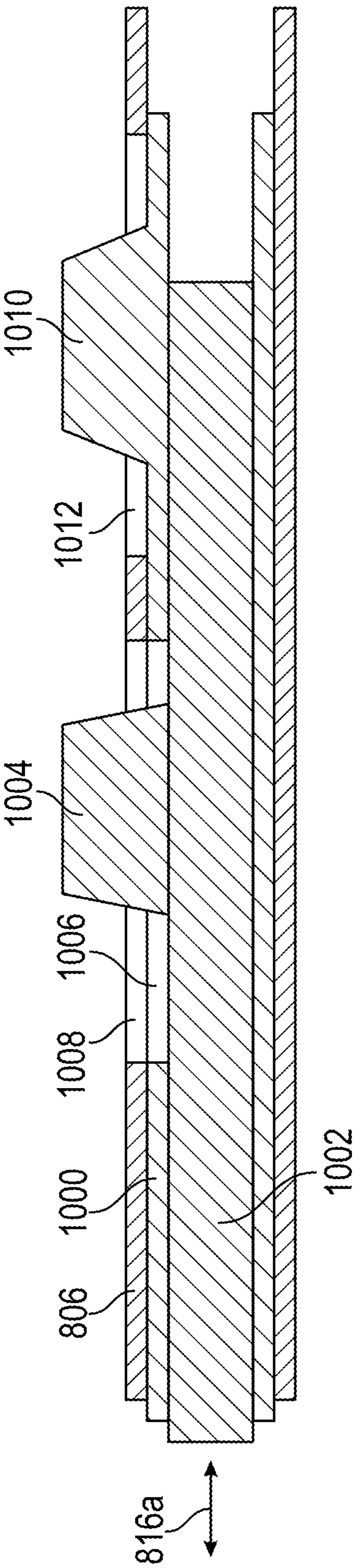
FIG. 10 is a cross-sectional view illustrating a mechanism for actuating the arcuate scrapers of the grasping structure of FIGS. 8A and 8B, in accordance with certain embodiments.

FIG. 10 illustrates an example mechanism for coupling the slider 808 and deformable basket 810 to the arms 812, 814 or coupling the slider 808 and slider 900 to the arms 812, 814. The illustrated mechanism is exemplary only and shows an example relative movement of components. Further, the actual size and relative position of components may vary. For purposes of FIG. 10, "first actuator" and "second actuator" refer to the slider 808 and deformable basket 810, or vice versa. The "first actuator" and "second actuator" may also refer to the slider 808 and the slider 900, or vice versa.

In the illustrated embodiment, there are two slidable components 1000, 1002. The slidable components may be concentric tubes: slidable component 1002 being positioned within slidable component 1000. However, other arrangements are possible, such as the slidable components simply being positioned adjacent one another within the outer tube 806 or a cavity within the handle 802. The slidable component 1000 may be coupled to the outer arm 812 whereas the slidable component 1002 is coupled to the inner arm 814. However, the opposite arrangement is also possible.

The slidable component 1002 is coupled to a mounting structure 1004 coupled to the first actuator. Where the slidable component 1002 is positioned within the slidable component 1000 embodied as a tube, the slidable component 1000 may define a slot 1006 through which the mounting structure 1004 protrudes and within which the mounting structure 1004 may slide along a range of motion along the longitudinal direction 816*a*. Where the slidable component 1002 is positioned within the outer tube 806, the outer tube 806 may define a slot 1008 through which the mounting structure 1004 protrudes and along which the mounting structure 1004 has a range of motion along the longitudinal direction 816*a*.

The slidable component 1000 is coupled to a mounting structure 1010 coupled to the second actuator. Where the slidable component 1000 is positioned within the outer tube 806, the mounting structure 1010 may also protrude through the slot 1008 and have a range of motion along the longitudinal direction 816*a* within the slot 1008. Alternatively, the mounting structure 1010 may protrude through a different slot.

A first direction may be defined as movement outwardly from the distal end of the outer tube 806 and a second direction may be defined as movement inwardly into the distal end of the outer tube 806. Moving the first actuator in the first direction (e.g., by sliding a slider or compressing a deformable basket) extends the outer arm 812 from the outer tube 806. Where the slidable component 1002 is mounted within the slidable component 1000, there may be a degree of friction or interference with an end (right end in the illustrated orientation) of the slot 1006 that causes the inner arm 814 to extend outwardly simultaneously with the outer arm 812. The second actuator may be used to urge the slidable component in the second direction prior to moving the first actuator in the first direction such that when the outer arm 812 and inner arm 814 are simultaneously extended, a gap will be present between the scrapers 812*b*, 814*b* along the longitudinal direction 816*a* (see FIG. 11B, discussed below). The length of the slot 1006 may be selected to control the size of the gap. The second actuator may be moved in the first direction after the outer arm 812 is extended to extend the inner arm 814 to the point that the scrapers 812*b*, 814*b* are pressed together. The first actuator, or both the first actuator and the second actuator, may then be moved in the second direction to draw the arms 812, 814 into the outer tube 806. In some implementations, engagement of the scraper 812*b* with the scraper 814*b* and friction between the slidable components 1000, 1002 may be sufficient to push the inner arm 814 into the outer tube 806 when only the first actuator is used. In other implementations, a user may simultaneously engage both the first actuator and the second actuator when withdrawing the inner arm 814 and outer arm 812.

An alternative implementation to that shown in FIG. 10 is one in which the outer arm 812 is fixed relative to the handle 802 and the outer tube 806 is slidable relative to the handle 802 and coupled to the first actuator. In use, the user would withdraw the outer tube 806 by moving the first actuator in the second direction such that the scrapers 812*b*, 814*b* are extended from the distal end of the outer tube 806. After raising a flap with the scraper 812*b*, the second actuator may be moved in the first direction to press the scraper 814*b* against the scraper 812*b*. The first actuator may then be moved in the first direction to extend the outer tube 806 over the scrapers 812*b*, 814*b*.

Figure 11A:
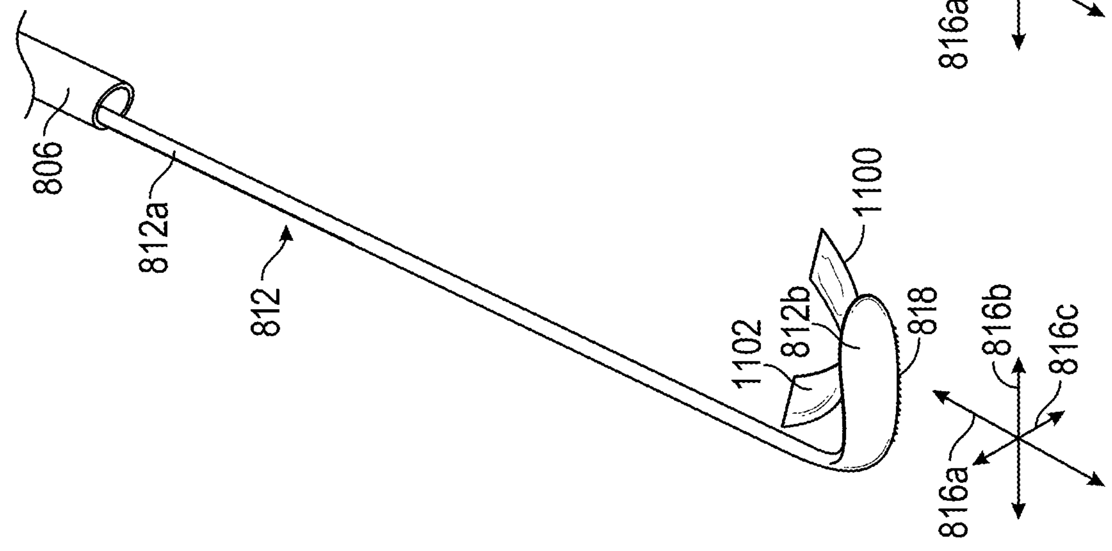
FIG. 11A is an isometric view showing a single arcuate scraper of FIGS. 8A and 8B extended, in accordance with certain embodiments.

Referring to FIG. 11A, after the outer tube 806 is inserted through a trocar cannula, the scraper 812*b* of the outer arm 812 may be extended from the outer tube 806 and pressed against a membrane 1100. The straight portion 812*a* and the scraper 812*b* itself may be sufficiently flexible such that pressure exerted on the membrane 1100 will cause the lower edge of the scraper 812*b* to be substantially completely (e.g., at least 80 percent) in contact with the membrane 1100. The scraper 812*b* may then be scraped across the membrane 1100 in order to raise a flap 1102. Drawing the scraper 812*b* across the membrane 1100 may simply raise the flap 1102 or both raise the flap and tear the membrane 1100.

Figure 11B:
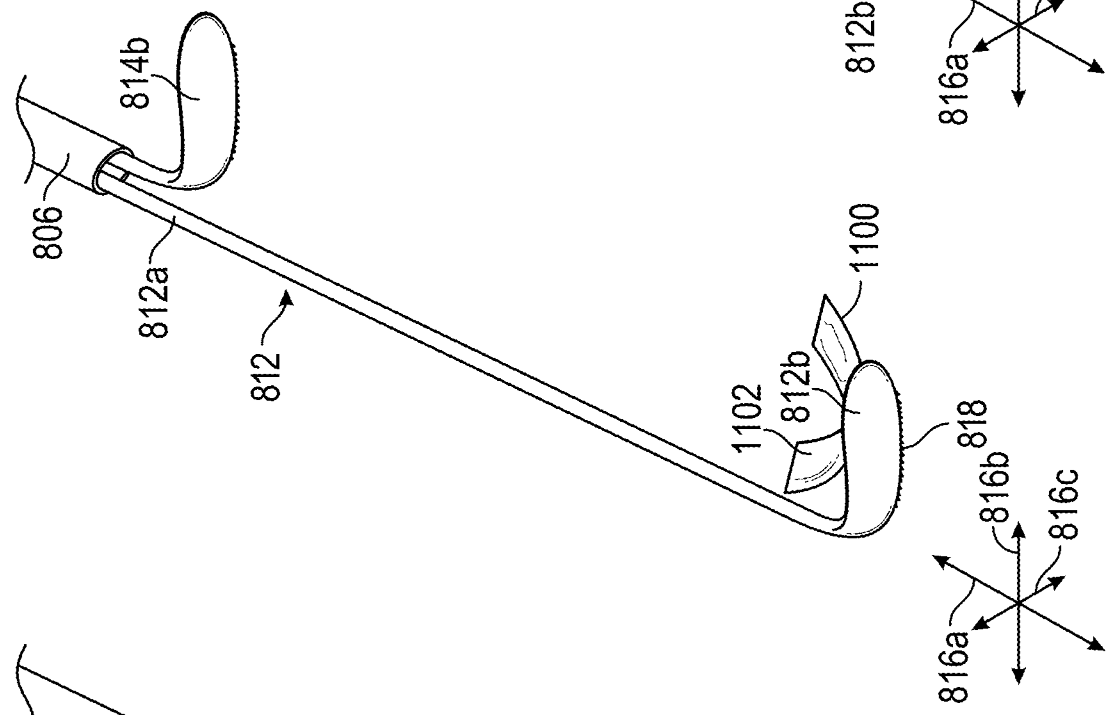
FIG. 11B is an isometric view showing both arcuate scrapers of FIGS. 8A and 8B extended but offset from one another, in accordance with certain embodiments.

Referring to FIG. 11B, the scraper 814*b* of the inner arm 814 may then be extended from the outer tube 806. Note that both scrapers 812*b*, 814*b* may be extended simultaneously prior to the scraping step shown in FIG. 11A provided that a gap between the scrapers 812*b*, 814*b* the longitudinal direction 816*a* is sufficient that only the scraper 812*b* is in contact with the membrane 1100 during the scraping step.

Figure 11C:
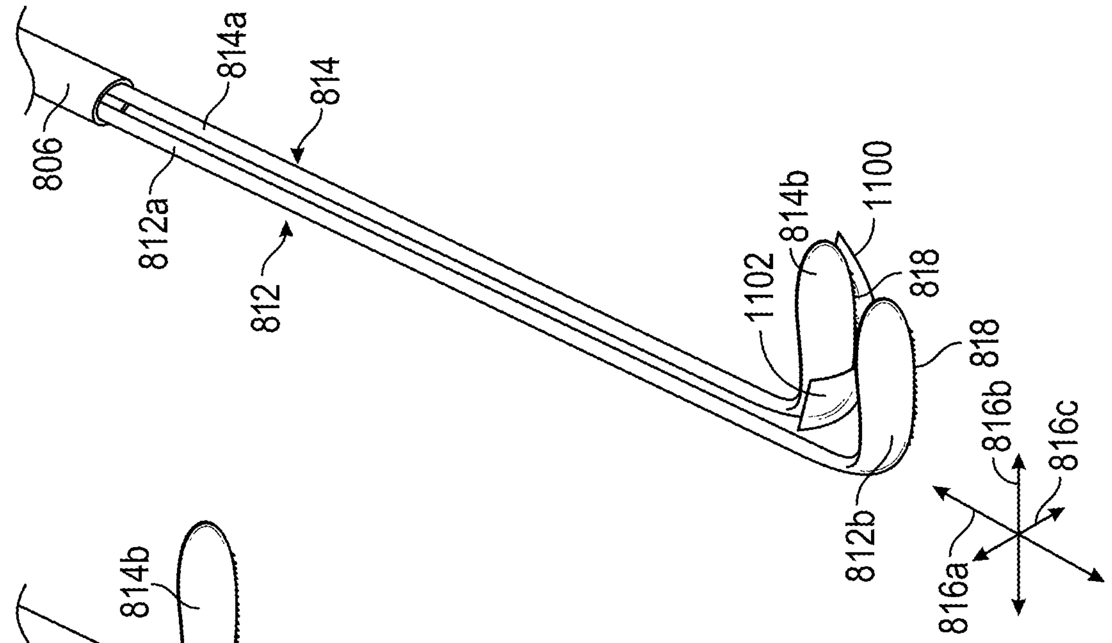
FIG. 11C is an isometric view showing the arcuate scrapers of FIGS. 8A and 8B brought together for grasping a flap of a membrane, in accordance with certain embodiments.

Referring to FIG. 11C, the inner arm 814 may continue to be extended from the outer tube 806 until the scraper 814*b* is pressed against the flap 1102 and the flap 1102 is gripped between the scrapers 812*b*, 814*b*. As the scraper 814*b* is extended from the outer tube 806, the barbs 818 on the lower edge of the scraper 814*b* may be pressed against the membrane 1100 and assist to further raise the flap 1102 until the scraper 814*b* is pressing the flap 1102 against the scraper 812*b*. Alternatively, barbs 818 may be omitted from the scraper 814*b*.

Figure 12:
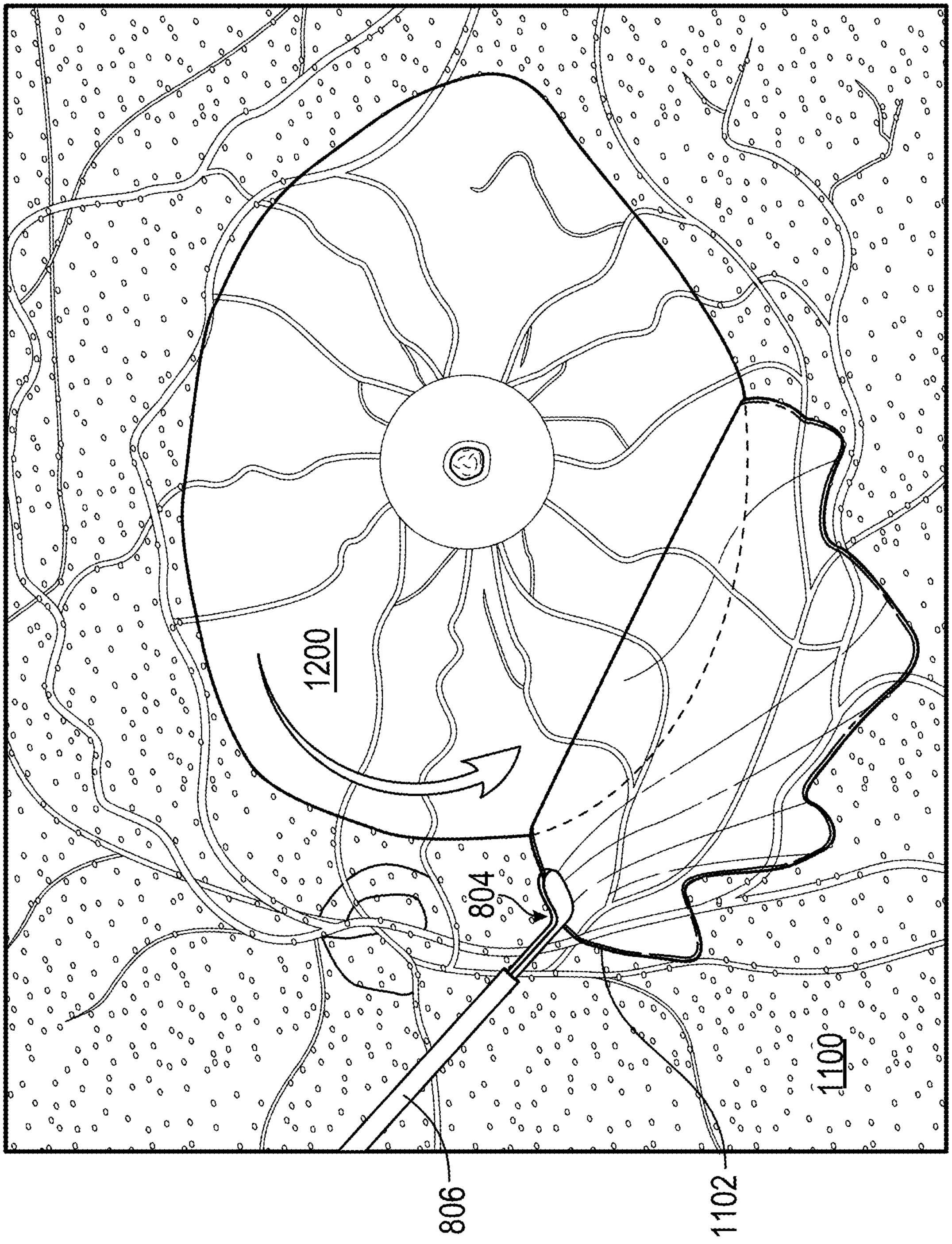
FIG. 12 is an isometric view showing an ILM being peeled using the grasping structure of FIGS. 8A and 8B, in accordance with certain embodiments.

Referring to FIG. 12, once the flap 1102 is grasped between the scrapers 812*b*, 814*b*, the grasping structure 804 may be moved in a circular motion in order to peel a portion of the membrane 1100 away from the retina 1200 of the patient. The scrapers 812*b*, 814*b* may then be withdrawn within the outer tube 806 and the outer tube 806 may be withdrawn from the trocar cannula.

Example Embodiments

Embodiment 1: A method for peeling a membrane from a retina of a patient's eye, the method comprising: inserting a distal end of an outer tube through a cannula in the patient's eye; extending an outer loop and an inner loop from the outer tube; engaging the membrane with the outer loop to form a flap; and bringing the inner loop and outer loop together such that the flap is grasped between the inner loop and the outer loop.

Embodiment 2: The method of Embodiment 1, further comprising pulling on the flap effective to peel a portion of the membrane from the retina.

Embodiment 3: The method of Embodiment 1, wherein the outer tube is mounted to a handle having an actuator mounted thereto and coupled to the inner loop, the method comprising moving the actuator in order to move the inner loop toward the outer loop.

Embodiment 4: The method of Embodiment 3, wherein: the actuator is a first actuator and a second actuator is mounted to the handle; the outer tube is slidably mounted to the handle and coupled to the second actuator; and extending the outer loop and the inner loop comprises moving the second actuator to withdraw the outer tube.

Embodiment 5: The method of Embodiment 1, wherein the outer loop and the inner loop are at least four times wider than an outer diameter of the outer tube when extended from the outer tube.

Embodiment 6: The method of Embodiment 5, further comprising withdrawing the outer loop and the inner loop into the outer tube while only elastically deforming the outer loop and the inner loop.

Embodiment 7: The method of Embodiment 6, wherein the outer loop and the inner loop each comprise nitinol.

Embodiment 8: An ophthalmic surgical instrument for peeling a retinal membrane, comprising: a handle; an actuator mounted on the handle; an outer tube having a proximal end mounted to the handle; an outer loop extending outwardly from a distal end of the outer tube; and an inner loop extending outwardly from the distal end of the outer tube and positioned within the outer loop, the actuator configured to move one of the inner loop and the outer loop such that the inner loop and outer loop are brought together to grasp the retinal membrane.

Embodiment 9: The ophthalmic surgical instrument of Embodiment 8, wherein the actuator is configured to move the inner loop toward the outer loop responsive to movement of the actuator in a first direction.

Embodiment 10: The ophthalmic surgical instrument of Embodiment 9, wherein the actuator is configured to move the inner loop away from the outer loop responsive to movement of the actuator in a second direction opposite the first direction.

Embodiment 11: The ophthalmic surgical instrument of Embodiment 8, wherein the outer loop and the inner loop are at least two times wider than an outer diameter of the outer tube.

Embodiment 12: The ophthalmic surgical instrument of Embodiment 11, wherein the outer loop and the inner loop are at least four times wider than an outer diameter of the outer tube.

Embodiment 13: The ophthalmic surgical instrument of Embodiment 12, wherein the outer loop and the inner loop are configured to elastically deform sufficiently to fit within the outer tube.

Embodiment 14: The ophthalmic surgical instrument of Embodiment 12, wherein the outer loop and the inner loop each comprise nitinol.

Embodiment 15: The ophthalmic surgical instrument of Embodiment 8, wherein a first surface of the outer loop includes first tapered barbs configured to grip a membrane on a retina of a patient's eye and having a length outward from the first surface that is less than a thickness of the membrane.

Embodiment 16: The ophthalmic surgical instrument of Embodiment 15, wherein the length is between 0.8 and 8 microns.

Embodiment 17: The ophthalmic surgical instrument of Embodiment 16, wherein a second surface of the inner loop positioned to engage the membrane when the first surface is pressed against the retina does not have barbs formed thereon.

Embodiment 18: The ophthalmic surgical instrument of Embodiment 8, wherein one of: the outer loop defines one or more slots and the inner loop defines one or more protrusions positioned within the one or more slots; and the inner loop defines the one or more slots and the outer loop defines the one or more protrusions positioned within the one or more slots.

Embodiment 19: The ophthalmic surgical instrument of Embodiment 8, wherein the outer loop defines an end portion, the end portion coupled to the distal end of the outer tube by flexible portions having greater flexibility than the end portion.

Embodiment 20: The ophthalmic surgical instrument of Embodiment 8, wherein: the actuator is a first actuator; the ophthalmic surgical instrument further comprising a second actuator coupled to the outer tube; and the outer tube is slidable relative to the handle, the outer loop, and the inner loop.

Embodiment 21: The ophthalmic surgical instrument of Embodiment 20, further comprising an inner tube positioned within the outer tube, the inner tube being fixed relative to the handle, the outer loop being fastened to the inner tube.

Embodiment 22: The ophthalmic surgical instrument of Embodiment 21, further comprising an inner rod positioned within the inner tube, the inner rod being coupled to the first actuator and the inner loop being fastened to the inner rod.

Embodiment 23: A method for peeling a membrane from a retina of a patient's eye, the method comprising: inserting a distal end of an outer tube through a cannula in the patient's eye, the outer tube mounted to a handle; extending an outer arm having an outer scraper secured thereto from the outer tube; engaging the membrane with the outer scraper to form a flap; extending an inner arm from the outer tube, the inner arm having an inner scraper secured thereto; and pressing the inner scraper toward the outer scraper such that the flap is grasped between the inner scraper and the outer scraper.

Embodiment 24: The method of Embodiment 23, wherein the inner arm, the outer arm, the inner scraper, and the outer scraper each comprise nitinol.

Embodiment 25: The method of Embodiment 23, wherein the outer scraper defines a concave surface and the inner scraper defines a convex surface, the method further comprising grasping the flap between the concave surface and the convex surface.

Embodiment 26: The method of Embodiment 23, wherein engaging the membrane with the outer scraper to form the flap comprises engaging the membrane with barbs formed on an edge of the outer scraper.

Embodiment 27: The method of Embodiment 26, wherein the barbs are oriented to pull the membrane toward the inner scraper.

Embodiment 28: The method of Embodiment 26, wherein the barbs have a length outward from the edge less than a thickness of the membrane.

Embodiment 29: An ophthalmic surgical instrument for peeling a retinal membrane, comprising: a handle; a first actuator mounted on the handle; a second actuator mounted on the handle; an outer tube having a proximal end mounted to the handle; an outer arm having an outer scraper secured thereto; and an inner arm having an inner scraper secured thereto; wherein the first actuator is configured to control extension of the outer arm from the outer tube and the second actuator is configured to control movement of the inner arm relative to the outer arm.

Embodiment 30: The ophthalmic surgical instrument of Embodiment 29, wherein the first actuator is coupled to the outer arm and the second actuator is coupled to the inner arm.

Embodiment 31: The ophthalmic surgical instrument of Embodiment 29, wherein the outer scraper defines a concave surface and the inner scraper defines a convex surface positioned to press against the concave surface.

Embodiment 32: The ophthalmic surgical instrument of Embodiment 31, wherein at least one of the concave surface and the convex surface is textured.

Embodiment 33: The ophthalmic surgical instrument of Embodiment 29, where the outer scraper has barbs formed on an edge thereof.

Embodiment 34: The ophthalmic surgical instrument of Embodiment 33, wherein the barbs are oriented to pull the retinal membrane toward the inner scraper.

Embodiment 35: The ophthalmic surgical instrument of Embodiment 33, wherein the barbs have a length outward from the edge less than a thickness of the retinal membrane.

Embodiment 36: The ophthalmic surgical instrument of Embodiment 35, wherein the length is between 1 and 3 microns.

Embodiment 37: The ophthalmic surgical instrument of Embodiment 29, wherein: the outer tube 106 defines a longitudinal direction parallel to an axis of symmetry of the outer tube 106; and the outer scraper extends outwardly in a transverse direction beyond an outer diameter of the outer tube, the transverse direction being perpendicular to the longitudinal direction.

Embodiment 38: The ophthalmic surgical instrument of Embodiment 37, wherein the outer scraper and the inner scraper extend outwardly in the transverse direction by at least two times the outer diameter of the outer tube.

Embodiment 39: The ophthalmic surgical instrument of Embodiment 29, wherein the outer arm, the inner arm, the outer scraper, and the inner scraper are made of nitinol.

Embodiment 40: A method for peeling a membrane from a retina of a patient's eye, the method comprising: inserting a distal end of an outer tube through a cannula in the patient's eye, the outer tube mounted to a handle; extending an outer arm having an outer scraper secured thereto from the outer tube; engaging the membrane with the outer scraper to form a flap; extending an inner arm from the outer tube, the inner arm having an inner scraper secured thereto; and pressing the inner scraper toward the outer scraper such that the flap is grasped between the inner scraper and the outer scraper.

Embodiment 41: The method of Embodiment 40, further comprising pulling on the flap effective to peel a portion of the membrane from the retina.

Embodiment 42: The method of Embodiment 40, wherein: a first actuator and a second actuator are mounted to the handle, the first actuator coupled to the outer arm and the second actuator coupled to the inner arm; extending the outer arm from the outer tube comprises moving the first actuator; and extending the inner arm from the outer tube comprises moving the second actuator.

Embodiment 43: The method of Embodiment 40, wherein the outer scraper and the inner scraper extend outwardly from an axis of symmetry of the outer tube by at least two times a diameter of the outer tube.

The foregoing description is provided to enable any person skilled in the art to practice the various embodiments described herein. Various modifications to these embodiments will be readily apparent to those skilled in the art, and the generic principles defined herein may be applied to other embodiments. Thus, the claims are not intended to be limited to the embodiments shown herein, but are to be accorded the full scope consistent with the language of the claims.

What is claimed is:

1. An ophthalmic surgical instrument for peeling a retinal membrane, comprising:

a handle;

at least one actuator mounted on the handle;

an outer tube having a proximal end mounted to the handle;

a flexible outer grasping member extending outwardly from a distal end of the outer tube or configured to extend outwardly from the distal end of the outer tube, the flexible outer grasping member comprising straight portions connected to one another by a rounded end portion; and a flexible inner grasping member extending outwardly from the distal end of the outer tube or configured to extend outwardly from the distal end of the outer tube, the flexible inner grasping member comprising straight portions connected to one another by a rounded end portion, wherein:

the straight portions of the flexible outer grasping member and the flexible inner grasping member are aligned along a longitudinal plane, the rounded end portions of the flexible outer grasping member and the flexible inner grasping member are angularly offset from the longitudinal plane, and the at least one actuator is configured to move at least one of the flexible outer grasping member or the flexible inner grasping member relative to the other such that the rounded end portions of the flexible inner grasping member and the flexible outer grasping member are brought together to grasp the retinal membrane.

2. The ophthalmic surgical instrument of claim 1, wherein:

the flexible outer grasping member comprises an outer loop extending outwardly from the distal end of the outer tube; and the flexible inner grasping member comprises an inner loop extending outwardly from the distal end of the outer tube and positioned within the outer loop.

3. The ophthalmic surgical instrument of claim 2, wherein the at least one actuator is configured to move the inner loop toward the outer loop responsive to movement of the at least one actuator in a first direction, and wherein the at least one actuator is further configured to move the inner loop away from the outer loop responsive to movement of the at least one actuator in a second direction opposite the first direction.

4. The ophthalmic surgical instrument of claim 2, wherein the outer loop and the inner loop are at least two times wider than an outer diameter of the outer tube.

5. The ophthalmic surgical instrument of claim 4, wherein the outer loop and the inner loop are configured to elastically deform sufficiently to fit within the outer tube.

6. The ophthalmic surgical instrument of claim 4, wherein the outer loop and the inner loop each comprise nitinol.

7. The ophthalmic surgical instrument of claim 2, wherein a first surface of the outer loop includes first tapered barbs configured to grip a membrane on a retina of a patient's eye, the first tapered barbs having a length outward from the first surface that is less than a thickness of the membrane.

8. The ophthalmic surgical instrument of claim 7, wherein a second surface of the inner loop positioned to engage the membrane when the first surface is pressed against the retina does not have barbs formed thereon.

* * * * *